(12) United States Patent
Cromack et al.

(10) Patent No.: US 8,257,724 B2
(45) Date of Patent: *Sep. 4, 2012

(54) DELIVERY OF HIGHLY LIPOPHILIC AGENTS VIA MEDICAL DEVICES

(75) Inventors: Keith R. Cromack, Gurnee, IL (US); John L. Toner, Libertyville, IL (US); Sandra E. Burke, Libertyville, IL (US); Richard W. Krasula, Libertyville, IL (US); Lewis B. Schwartz, Lake Forest, IL (US)

(73) Assignee: Abbott Laboratories, Abbott Park, IL (US)

( * ) Notice: Subject to any disclaimer, the term of this patent is extended or adjusted under 35 U.S.C. 154(b) by 1456 days.

This patent is subject to a terminal disclaimer.

(21) Appl. No.: 11/386,469

(22) Filed: Mar. 22, 2006

(65) Prior Publication Data

US 2006/0228452 A1    Oct. 12, 2006

Related U.S. Application Data

(60) Continuation-in-part of application No. 10/796,243, filed on Mar. 9, 2004, now Pat. No. 7,445,792, and application No. 11/386,469, which is a continuation-in-part of application No. 10/977,288, filed on Oct. 29, 2004, now Pat. No. 7,399,480, which is a continuation-in-part of application No. 10/235,572, filed on Sep. 6, 2002, now abandoned, which is a continuation-in-part of application No. 09/950,307, filed on Sep. 10, 2001, now Pat. No. 6,890,546, which is a continuation-in-part of application No. 09/433,001, filed on Nov. 2, 1999, now Pat. No. 6,329,386, which is a division of application No. 09/159,945, filed on Sep. 24, 1998, now Pat. No. 6,015,815.

(60) Provisional application No. 60/453,555, filed on Mar. 10, 2003, provisional application No. 60/060,015, filed on Sep. 29, 1997, provisional application No. 60/664,328, filed on Mar. 23, 2005, provisional application No. 60/727,080, filed on Oct. 14, 2005, provisional application No. 60/726,878, filed on Oct. 14, 2005, provisional application No. 60/732,577, filed on Oct. 17, 2005, provisional application No. 60/727,196, filed on Oct. 14, 2005.

(51) Int. Cl.
  *A61F 2/00*    (2006.01)
(52) U.S. Cl. .......... 424/423; 514/291; 514/449
(58) Field of Classification Search .......... 424/423; 514/291, 449
  See application file for complete search history.

(56) References Cited

U.S. PATENT DOCUMENTS

| | | | |
|---|---|---|---|
| 3,929,992 A | 12/1975 | Sehgal |
| 3,993,749 A | 11/1976 | Sehgal |
| 4,316,885 A | 2/1982 | Rakhit |
| 4,401,653 A | 8/1983 | Eng |
| 4,650,803 A | 3/1987 | Stella |
| 4,885,171 A | 12/1989 | Surendra |
| 4,916,193 A | 4/1990 | Tang |
| 4,994,071 A | 2/1991 | MacGregor |
| 5,023,262 A | 6/1991 | Caufield |
| 5,092,877 A | 3/1992 | Pinchuk |
| 5,120,725 A | 6/1992 | Kao |
| 5,120,727 A | 6/1992 | Kao |
| 5,120,842 A | 6/1992 | Failli |
| 5,163,952 A | 11/1992 | Froix |
| 5,177,203 A | 1/1993 | Failli |
| 5,304,121 A | 4/1994 | Sahatjian |
| 5,447,724 A | 9/1995 | Helmus |
| 5,457,111 A | 10/1995 | Luly |
| 5,464,650 A | 11/1995 | Berg |
| 5,516,781 A | 5/1996 | Morris |
| 5,527,337 A | 6/1996 | Stack |
| 5,563,146 A | 10/1996 | Morris |
| 5,605,696 A | 2/1997 | Eury |
| 5,624,411 A | 4/1997 | Tuch |
| 5,646,160 A | 7/1997 | Morris |
| 5,665,728 A | 9/1997 | Morris |
| 5,705,583 A | 1/1998 | Bowers |

(Continued)

FOREIGN PATENT DOCUMENTS

EP    0184162 A2    6/1986

(Continued)

OTHER PUBLICATIONS

Clark, Meta-Analysis: Secondary Prevention Programs for Patients with Coronary Artery Disease, Annals or Internal Medicine, vol. 143, pp. 659-672, 2005.*

Lincoff (Sustained local delivery of dexamethasone by a novel intravascular eluting stent to prevent restenosis in the porcine coronary injury model, J. Am. Coll. Cardiol. vol. 29, No. 4, pp. 808-816, Mar. 15, 1997).*

International Search Report for application PCT/US2007/007357, mailed Jul. 23, 2008, 13 pgs.

(Continued)

*Primary Examiner* — Benjamin Packard
*Assistant Examiner* — Adam C Milligan
(74) *Attorney, Agent, or Firm* — Squire Sanders (US) LLP

(57) ABSTRACT

An apparatus and system for delivering a lipophilic agent associated with a medical device including: a medical device, a first lipophilic agent capable of penetrating a body lumen, wherein the transfer coefficients of the first lipophilic agent is by an amount that is statistically significant of at least approximately 5,000, wherein the first lipophilic agent is associated with the medical device, wherein the first lipophilic agent/medical device is placed adjacent to said body lumen, and wherein a therapeutically effective amount of the first lipophilic agent is delivered to a desired area within a subject. Furthermore, the invention relates to a method for improving patency in a subject involving placement of a medical device in a body lumen for treating and/or preventing adjacent diseases or maintaining patency of the body lumen.

33 Claims, 23 Drawing Sheets

U.S. PATENT DOCUMENTS

| | | | | |
|---|---|---|---|---|
| 5,716,981 | A | * | 2/1998 | Hunter et al. .................. 514/449 |
| 6,015,815 | A | * | 1/2000 | Mollison ....................... 514/291 |
| 6,090,901 | A | | 7/2000 | Bowers |
| 6,273,913 | B1 | | 8/2001 | Wright |
| 6,284,305 | B1 | | 9/2001 | Ding |
| 6,358,556 | B1 | | 3/2002 | Ding |
| 6,413,272 | B1 | | 7/2002 | Igaki |
| 6,419,692 | B1 | | 7/2002 | Yang |
| 6,585,764 | B2 | | 7/2003 | Wright |
| 2003/0129215 | A1 | | 7/2003 | Mollison |
| 2003/0181973 | A1 | | 9/2003 | Sahota |
| 2005/0004661 | A1 | | 1/2005 | Lewis |

FOREIGN PATENT DOCUMENTS

| | | |
|---|---|---|
| EP | 0467606 A1 | 1/1992 |
| WO | 92/05179 | 4/1992 |
| WO | 01/87372 A1 | 11/2001 |
| WO | 02/055122 A1 | 7/2002 |
| WO | WO 03/022807 | 3/2003 |
| WO | WO 2004/022124 | 3/2004 |
| WO | WO 2006/102359 | 9/2006 |
| WO | WO 2007/111885 | 10/2007 |
| WO | WO 2007/112006 | 10/2007 |

OTHER PUBLICATIONS

Aggarwal, A., D.J. Schneider, B.E. Sobel, and H.L. Dauerman. 2003. Comparison of inflammatory markers in patients with diabetes mellitus versus those without before and after coronary arterial stenting. Am J Cardiol. 92:924-9.

Baker, H., A. Sidorowicz, S.N. Sehgal, and C. Vezina. 1978. Rapamycin (AY-22,989), a new antifungal antibiotic. III. In vitro and in vivo evaluation. J Antibiot (Tokyo). 31:539-45.

Bierer, B.E., S.L. Schreiber, and S.J. Burakoff. 1991. The effect of the immunosuppressant FK-506 on alternate pathways of T cell activation. Eur J Immunol. 21:439-45.

Biondi-Zoccai, G.G., A. Abbate, G. Liuzzo, and L.M. Biasucci. 2003. Atherothrombosis, inflammation, and diabetes. J Am Coll Cardiol. 41:1071-7.

Brown, E.J., M.W. Albers, T.B. Shin, K. Ichikawa, C.T. Keith, W.S. Lane, and S.L. Schreiber. 1994. A mammalian protein targeted by G1-arresting rapamycin-receptor complex. Nature. 369:756-8.

Bunchman, T.E., and C.A. Brookshire. 1991. Smooth muscle cell proliferation by conditioned media from cyclosporine-treated endothelial cells: a role of endothelin. Transplant Proc. 23:967-8.

Carter, A.J., M. Aggarwal, G.A. Kopia, F. Tio, P.S. Tsao, R. Kolata, A.C. Yeung, G. Llanos, J. Dooley, and R. Falotico. 2004. Long-term effects of polymer-based, slow-release, sirolimus-eluting stents in a porcine coronary model. Cardiovasc Res. 63:617-24.

Dandona, P., and A. Aljada. 2002. A rational approach to pathogenesis and treatment of type 2 diabetes mellitus, insulin resistance, inflammation, and atherosclerosis. Am J Cardiol. 90:27G-33G.

Dumont, F.J., M.R. Melino, M.J. Staruch, S.L. Koprak, P.A. Fischer, and N.H. Sigal. 1990. The immunosuppressive macrolides FK-506 and rapamycin act as reciprocal antagonists in murine T cells. J Immunol. 144:1418-24.

Fretz, H., M. Albers, A. Gala, R. Standaert, W. Lane, S. Burakoff, B. Bierer, and S. Schreiber. 1991. Rapamycin and FK506 binding proteins (immunophilins). J. Am. Chem. Soc. 113:1409-1411.

Grech, E.D., and D.R. Ramsdale. 2003. Acute coronary syndrome: unstable angina and non-ST segment elevation myocardial infarction. British Med. J. 326:1259-61.

Harding, M.W., A. Galat, D.E. Uehling, and S.L. Schreiber. 1989. A receptor for the immunosuppressant FK506 is a cis-trans peptidyl-prolyl isomerase. Nature. 341:758-60.

Hayward, C., D. Yohannes, and S. Danishefsky. 1993. Total synthesis of rapamycin via a novel titanium-mediated aldol macrocyclization reaction. J. Am. Chem. Soc. 115:9345-9346.

Helmus, M. 1990. Medical Device Design—A Systems Approach: Central Venous Catheters. In 22nd International Society for the Advancement of Material and Process Engineering Technical Conference.

Ji, Q., M. Reimer, and T. El-Shourbagy. 2004. 96-well liquid—liquid extraction liquid chromatography-tandem mass spectrometry method for the quantitative determination of ABT-578 in human blood samples. Journal of Chromatography B. 805:67-75.

Kino, T., N. Inamura, F. Sakai, K. Nakahara, T. Goto, M. Okuhara, M. Kohsaka, H. Aoki, and T. Ochiai. 1987. Effect of FK-506 on human mixed lymphocyte reaction in vitro. Transplant Proc. 19:36-9.

Kornowski, R., M.K. Hong, F.O. Tio, O. Bramwell, H. Wu, and M.B. Leon. 1998. In-stent restenosis: contributions of inflammatory responses and arterial injury to neointimal hyperplasia. J Am Coll Cardiol. 31:224-30.

Martel, R.R., J. Klicius, and S. Galet. 1977. Inhibition of the immune response by rapamycin, a new antifungal antibiotic. Can J Physiol Pharmacol. 55:48-51.

Morris, R. 1992. Rapamycins: antifungal, antitumor, antiproliferative, and immunosuppressive macrolides. Transplant. Rev. 6:39-87.

Morris, R., and B. Meiser. 1989. Identification of a new pharmacologic action for an old compound. Med. Sci. Res. 17:609.

Nicolaou, K., T. Chakraborty, A. Piscopio, N. Minowa, and P. Bertinato. 1993. Total synthesis of rapamycin. J. Am. Chem. Soc. 115:4419-4420.

Paiva, N.L., A.L. Demain, and M.F. Roberts. 1991. Incorporation of acetate, propionate, and methionine into rapamycin by *Streptomyces hygroscopicus*. J Nat Prod. 54:167-77.

Roffi, M., and E.J. Topol. 2004. Percutaneous coronary intervention in diabetic patients with non-ST-segment elevation acute coronary syndromes. Eur Heart J. 25:190-8.

Romo, D., S. Meyer, D. Johsnon, and S. Schrieber. 1993. Total synthesis of (-)-rapamycin using an Evans-Tishchenko fragment coupling. J. Am. Chem. Soc. 115:7906-7907.

Sabatini, D.M., H. Erdjument-Bromage, M. Lui, P. Tempst, and S.H. Snyder. 1994. RAFT1: a mammalian protein that binds to FKBP12 in a rapamycin-dependent fashion and is homologous to yeast TORs. Cell. 78:35-43.

Schwartz, R. 1992. Restenosis and the proportional neointimal response to coronary artery injury: results in a porcine model. J Am Coll Cardiol. 19:267-274.

Sehgal, S.N., H. Baker, C.P. Eng, K. Singh, and C. Vezina. 1983. Demethoxyrapamycin (AY-24,668), a new antifungal antibiotic. J Antibiot (Tokyo). 36:351-4.

Sehgal, S.N., H. Baker, and C. Vezina. 1975. Rapamycin (AY-22,989), a new antifungal antibiotic. II. Fermentation, isolation and characterization. J Antibiot (Tokyo). 28:727-32.

Shichiri, M., Y. Hirata, T. Nakajima, K. Ando, T. Imai, M. Yanagisawa, T. Masaki, and F. Marumo. 1991. Endothelin-1 is an autocrine/paracrine growth factor for human cancer cell lines. J Clin Invest. 87:1867-71.

Siekierka, J.J., S.H. Hung, M. Poe, C.S. Lin, and N.H. Sigal. 1989. A cytosolic binding protein for the immunosuppressant FK506 has peptidyl-prolyl isomerase activity but is distinct from cyclophilin. Nature. 341:755-7.

Suzuki, T., G. Kopia, S. Hayashi, L.R. Bailey, G. Llanos, R. Wilensky, B.D. Klugherz, G. Papandreou, P. Narayan, M.B. Leon, A.C. Yeung, F. Tio, P.S. Tsao, R. Falotico, and A.J. Carter. 2001. Stent-based delivery of sirolimus reduces neointimal formation in a porcine coronary model. Circulation. 104:1188-93.

Vezina, C., A. Kudelski, and S.N. Sehgal. 1975. Rapamycin (AY-22,989), a new antifungal antibiotic. I. Taxonomy of the producing streptomycete and isolation of the active principle. J Antibiot (Tokyo). 28:721-6.

Yamagishi, S., C.C. Hsu, K. Kobayashi, and H. Yamamoto. 1993. Endothelin 1 mediates endothelial cell-dependent proliferation of vascular pericytes. Biochem Biophys Res Commun. 191:840-6.

Yudkin, J.S., M. Kumari, S.E. Humphries, and V. Mohamed-Ali. 2000. Inflammation, obesity, stress and coronary heart disease: is interleukin-6 the link? Atherosclerosis. 148:209-14.

* cited by examiner

DELIVERY OF HIGHLY LIPOPHILIC AGENTS VIA MEDICAL DEVICES

CROSS-REFERENCE TO RELATED APPLICATIONS

This application is a continuation-in-part of U.S. Ser. No. 10/796,243 filed Mar. 9, 2004 now U.S. Pat. No. 7,445,792, which claims priority to U.S. Ser. No. 60/453,555 filed Mar. 10, 2003 and this application is a continuation-in-part of U.S. Ser. No. 10/977,288 filed Oct. 29, 2004 now U.S. Pat. No. 7,399,480, which is a continuation-in-part of U.S. Ser. No. 10/235,572, filed Sep. 6, 2002 now abandoned, which is a continuation in part of U.S. Ser. No. 09/950,307, filed Sep. 10, 2001, now U.S. Pat. No. 6,890,546, which is a continuation-in-part of U.S. Ser. No. 09/433,001, filed Nov. 2, 1999, now U.S. Pat. No. 6,329,386, which is a divisional of U.S. Ser. No. 09/159,945, filed Sep. 24, 1998, now U.S. Pat. No. 6,015,815 and claims priority to U.S. Ser. No. 60/060,015, filed Sep. 26, 1997; this application also claims priority to U.S. Ser. No. 60/664,328 filed on Mar. 23, 2005, U.S. Ser. No. 60/727,080 filed Oct. 14, 2005, U.S. Ser. No. 60/726,878 filed Oct. 14, 2005, U.S. Ser. No. 60/732,577 filed Oct. 17, 2005, and U.S. Ser. No. 60/727,196 filed Oct. 14, 2005; the entirety of all the above of which is incorporated herein by reference.

FIELD OF THE INVENTION

The invention relates to apparatuses, systems, and methods of remote drug delivery of highly lipophilic agents utilizing medical devices, and more specifically, lipophilic agents having a transfer coefficient of at least approximately 5,000 (ug/mL)$^{-1}$.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Recently, several classes of macrocyclic compounds having potent immunomodulatory activity have been discovered. Okuhara et al., in European Patent Application No. 184,162, published Jun. 11, 1986, disclose a number of macrocyclic compounds isolated from the genus Streptomyces, including the immunosuppressant FK-506, a 23-membered macrocyclic lactone, which was isolated from a strain of S. tsukubaensis.

Other related natural products, such as FR-900520 and FR-900523, which differ from FK-506 in their alkyl substituent at C-21, have been isolated from S. hygroscopicus yakushimnaensis. Another analog, FR-900525, produced by S. tsukubaensis, differs from FK-506 in the replacement of a pipecolic acid moiety with a proline group. Unsatisfactory side-effects associated with cyclosporine and FK-506 such as nephrotoxicity, have led to a continued search for immunosuppressant compounds having improved efficacy and safety, including an immunosuppressive agent which is effective topically, but ineffective systemically (U.S. Pat. No. 5,457,111).

Rapamycin is a macrocyclic triene antibiotic produced by Streptomyces hygroscopicus, which was found to have antifungal activity, particularly against Candida albicans, both in vitro and in vivo (C. Vezina et al., J. Antibiot. 1975, 28, 721; S. N. Sehgal et al., J. Antibiot. 1975, 28, 727; H. A. Baker et al., J. Antibiot. 1978, 31, 539; U.S. Pat. No. 3,929,992; and U.S. Pat. No. 3,993,749).

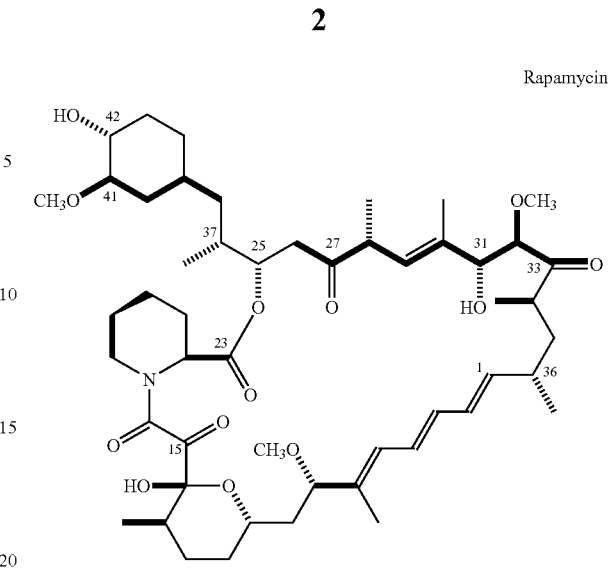

Rapamycin

Rapamycin alone (U.S. Pat. No. 4,885,171) or in combination with picibanil (U.S. Pat. No. 4,401,653) has been shown to have antitumor activity. In 1977, rapamycin was also shown to be effective as an immunosuppressant in the experimental allergic encephalomyelitis model, a model for multiple sclerosis; in the adjuvant arthritis model, a model for rheumatoid arthritis; and was shown to effectively inhibit the formation of IgE-like antibodies (R. Martel et al., Can. J. Physiol. Pharmacol., 1977, 55, 48).

The immunosuppressive effects of rapamycin have also been disclosed in FASEB, 1989, 3, 3411 as has its ability to prolong survival time of organ grafts in histoincompatible rodents (R. Morris, Med. Sci. Res., 1989, 17, 877). The ability of rapamycin to inhibit T-cell activation was disclosed by M. Strauch (FASEB, 1989, 3, 3411). These and other biological effects of rapamycin are reviewed in Transplantation Reviews, 1992, 6, 39-87.

Rapamycin has been shown to reduce neointimal proliferation in animal models, and to reduce the rate of restenosis in humans. Evidence has been published showing that rapamycin also exhibits an anti-inflammatory effect, a characteristic which supported its selection as an agent for the treatment of rheumatoid arthritis. Because both cell proliferation and inflammation are thought to be causative factors in the formation of restenotic lesions after balloon angioplasty and stent placement, rapamycin and analogs thereof have been proposed for the prevention of restenosis.

Ester and diester derivatives of rapamycin (esterification at positions 31 and 42) have been shown to be useful as antifungal agents (U.S. Pat. No. 4,316,885) and as water soluble prodrugs of rapamycin (U.S. Pat. No. 4,650,803).

Fermentation and purification of rapamycin and 30-demethoxy rapamycin have been described in the literature (C. Vezina et al. J. Antibiot. (Tokyo), 1975, 28 (10), 721; S. N. Sehgal et al., J. Antibiot. (Tokyo), 1975, 28(10), 727; 1983, 36(4), 351; N. L. Pavia et al., J. Natural Products, 1991, 54(1), 167-177).

Numerous chemical modifications of rapamycin have been attempted. These include the preparation of ester and diester derivatives of rapamycin (WO 92/05179), 27-oximes of rapamycin (EP0 467606); 42-oxo analog of rapamycin (U.S. Pat. No. 5,023,262); bicyclic rapamycins (U.S. Pat. No. 5,120,725); rapamycin dimers (U.S. Pat. No. 5,120,727); silyl ethers of rapamycin (U.S. Pat. No. 5,120,842); and arylsulfonates and sulfamates (U.S. Pat. No. 5,177,203). Rapamycin was recently synthesized in its naturally occurring enantiomeric form (K. C. Nicolaou et al., *J. Am. Chem. Soc.,* 1993, 115, 4419-4420; S. L. Schreiber, *J. Am. Chem. Soc.,* 1993, 115, 7906-7907; S. J. Danishefsky, *J. Am. Chem. Soc.,* 1993, 115, 9345-9346.

It has been known that rapamycin, like FK-506, binds to FKBP-12 (Siekierka, J. J.; Hung, S. H. Y.; Poe, M.; Lin, C. S.; Sigal, N. H. *Nature,* 1989, 341, 755-757; Harding, M. W.; Galat, A.; Uehling, D. E.; Schreiber, S. L. *Nature* 1989, 341, 758-760; Dumont, F. J.; Melino, M. R.; Staruch, M. J.; Koprak, S. L.; Fischer, P. A.; Sigal, N. H. *J. Immunol.* 1990, 144, 1418-1424; Bierer, B. E.; Schreiber, S. L.; Burakoff, S. J. *Eur. J. Immunol.* 1991, 21, 439-445; Fretz, H.; Albers, M. W.; Galat, A.; Standaert, R. F.; Lane, W. S.; Burakoff, S. J.; Bierer, B. E.; Schreiber, S. L. *J. Am. Chem. Soc.* 1991, 113, 1409-1411). Recently it has been discovered that the rapamycin/FKBP-12 complex binds to yet another protein, which is distinct from calcineurin, the protein that the FK-506/FKBP-12 complex inhibits (Brown, E. J.; Albers, M. W.; Shin, T. B.; Ichikawa, K.; Keith, C. T.; Lane, W. S.; Schreiber, S. L. *Nature* 1994, 369, 756-758; Sabatini, D. M.; Erdjument-Bromage, H.; Lui, M.; Tempest, P.; Snyder, S. H. *Cell,* 1994, 78, 35-43).

Percutaneous transluminal coronary angioplasty (PTCA) was developed by Andreas Gruntzig in the 1970's. The first canine coronary dilation was performed on Sep. 24, 1975; studies showing the use of PTCA were presented at the annual meetings of the American Heart Association the following year. Shortly thereafter, the first human patient was studied in Zurich, Switzerland, followed by the first American human patients in San Francisco and New York. While this procedure changed the practice of interventional cardiology with respect to treatment of patients with obstructive coronary artery disease, the procedure did not provide long-term solutions. Patients received only temporary abatement of the chest pain associated with vascular occlusion; repeat procedures were often necessary. It was determined that the existence of restenotic lesions severely limited the usefulness of the new procedure. In the late 1980's, stents were introduced to maintain vessel patency after angioplasty. Stenting is involved in 90% of angioplasty performed today. Before the introduction of stents, the rate of restenosis ranged from 30% to 50% of the patients who were treated with balloon angioplasty. The recurrence rate after dilatation of in-stent restenosis may be as high as 70% in selected patient subsets, while the angiographic restenosis rate in de novo stent placement is about 20%. Placement of the stent reduced the restenosis rate to 15% to 20%. This percentage likely represents the best results obtainable with purely mechanical stenting. The restenotic lesion is caused primarily by neointimal hyperplasia, which is distinctly different from atherosclerotic disease both in time-course and in histopathologic appearance. Restenosis is a healing process of damaged coronary arterial walls, with neointimal tissue impinging significantly on the vessel lumen. Vascular brachytherapy appears to be efficacious against in-stent restenotic lesions. Radiation, however, has limitations of practicality and expense, and lingering questions about safety and durability.

Accordingly, it is desired to reduce the rate of restenosis by at least 50% of its current level. It is for this reason that a major effort is underway by the interventional device community to fabricate and evaluate drug-eluting stents. Such devices could have many advantages if they were successful, principally since such systems would need no auxiliary therapies, either in the form of periprocedural techniques or chronic oral pharmacotherapy.

In surgical or other related invasive medicinal procedures, the insertion of a medical device having an interventional component including stent devices in blood vessels, urinary tracts or other difficult to access places for the purpose of preventing restenosis, providing vessel or lumen wall support or reinforcement and for other therapeutic or restorative functions has become a common form of long-term treatment. Typically, such interventional components are applied to a location of interest utilizing a vascular catheter, or similar transluminal device, to carry the stent to the location of interest where it is thereafter released to expand or be expanded in situ. These devices are generally designed as permanent implants which may become incorporated in the vascular or other tissue that they contact at implantation.

Implanted interventional components including stents have also been used to carry medicinal agents, such as thrombolytic agents. U.S. Pat. No. 5,163,952 to Froix discloses a thermal memoried expanding plastic stent device that can be formulated to carry a medicinal agent by utilizing the material of the stent itself as an inert polymeric drug carrier. Drug elution rates from a drug-loaded coating containing a hydrophilic (or lipophobic) drug are usually very fast initially when the coated device contacts body fluid or blood. Thus, an ongoing problem for drug delivery stents is achieving therapeutic drug concentrations at a target site within the body with minimal losses and systemic side effects. One technique to reduce the so-called burst effect is to add a membrane containing porosigen over the coating layer containing the biologically active material, as described for example in U.S. Pat. Nos. 5,605,696 and 5,447,724. Polymers are also used on stents as drug release coatings, as taught for example in U.S. Pat. No. 6,419,692. U.S. Pat. No. 6,284,305 describes elastomer coated implants in which the elastomer overcoat to control release of biologically active agent from an undercoat applied to a stent. U.S. Pat. No. 5,624,411 discloses a porous polymer on a stent to control the administration of a drug. WO 0187372 describes a stent coated with a polymer loaded with a combination of drugs, including rapamycin and dexamethasone. Pinchuk, in U.S. Pat. No. 5,092,877, discloses a stent of a polymeric material that may be employed with a coating associated with the delivery of drugs. Other patents which are directed to devices of the class utilizing biodegradable or biosorbable polymers include Tang et al, U.S. Pat. No. 4,916, 193 and MacGregor, U.S. Pat. No. 4,994,071. Sahatjian in U.S. Pat. No. 5,304,121, discloses a coating applied to a stent consisting of a hydrogel polymer and a preselected drug; possible drugs include cell growth inhibitors and heparin. A further method of making a coated intravascular stent carrying a therapeutic material in which a polymer coating is dissolved in a solvent and the therapeutic material dispersed in the solvent and the solvent thereafter evaporated is described in Berg et al, U.S. Pat. No. 5,464,650.

An article by Michael N. Helmus entitled "Medical Device Design—A Systems Approach: Central Venous Catheters", 22nd International Society for the Advancement of Material and Process Engineering Technical Conference (1990) relates to polymer/drug/membrane systems for releasing heparin. Those polymer/drug/membrane systems require two distinct layers to function. Ding et al., U.S. Pat. No. 6,358,556 described a process for coating a stent prosthesis using a biostable hydrophobic elastomer in which biologically active species are incorporated within a cured coating. In these coatings, the amount of polymer is relatively high, for example about 70% of the drug-loaded coating.

Thus, there remains a need for improved controlled delivery of a hydrophilic beneficial agent from a medical device, wherein the medical device reduces the burst effect and allows prolonged delivery of the beneficial agent without the side effects associated with some hydrophobic coatings. Also, there exists a need for a medical device with improved control of local release of two or more beneficial agents. Further, a need exists for a medical device that is capable of releasing a beneficial agent or agents immediately or soon after delivery followed by the controlled delivery of the same or other beneficial agents over prolonged time periods.

Previous drug eluting stents have been constructed to deliver therapeutic agents predominantly to the tissue immediately adjacent to the site of stent placement. The objective has been to control neointimal formation and allow the coronary vascular system to achieve rapid healing. Consequently, the bulk of the drug or drugs delivered is either present in the vascular tissue adjacent to the site of stent implantation, stays on the stent for prolonged periods, or is released into the blood stream. There is an unmet need for agents and devices which offer deep penetration of beneficial agents to tissues not immediately adjacent to the device. For example, delivery of a drug from a stent which not only delivers drug to the adjacent tissue, but also penetrates the myocardium and provides therapeutically useful doses of drug to a wide volume of tissue is particularly attractive.

SUMMARY OF THE INVENTION

The invention relates to a system for delivering a lipophilic agent including: a medical device, a first lipophilic agent capable of penetrating a body lumen, wherein the transfer coefficient of the first lipophilic agent is by an amount of at least approximately 5,000 $(ug/mL)^{-1}$, wherein the first lipophilic agent is associated with the medical device, wherein the first lipophilic agent/medical device is placed adjacent to said body lumen, and wherein a therapeutically effective amount of the first lipophilic agent is delivered to a desired area within a subject.

Another aspect of the invention relates to a method for improving patency in a subject involving placement of a medical device in a body lumen for treating and/or preventing adjacent diseases or maintaining patency of the body lumen including: providing a medical device in a body lumen, providing a first lipophilic agent capable of penetrating a body lumen, wherein the transfer coefficient of the first lipophilic agent is by an amount of at least approximately 5,000 $(ug/mL)^{-1}$, wherein the first lipophilic agent is associated with the medical device, placing the first lipophilic agent/medical device adjacent to a body lumen, and delivering a therapeutically effective amount of the first lipophilic agent to a desired area within a subject.

Yet another aspect of the invention relates to a medical device including: a therapeutically effective amount of a first lipophilic agent associated with the medical device, wherein the first lipophilic agent is capable of penetrating a body lumen, wherein the transfer coefficient of the first lipophilic agent is by an amount of at least approximately 5,000 $(ug/mL)^{-1}$, and wherein the first lipophilic agent/medical device is capable of being placed adjacent to a body lumen of a subjects and deliver a therapeutically effective amount of the first lipophilic agent to a desired area in a subject.

Still yet another aspect of the invention relates to a stent including: a therapeutically effective amount of a first lipophilic agent associated with the stent, wherein the first lipophilic agent is capable of penetrating a body lumen, wherein the transfer coefficient of the first lipophilic agent is by an amount of at least approximately 5,000 $(ug/mL)^{-1}$, and wherein the first lipophilic agent/stent is capable of being placed adjacent to a body lumen of a subject and deliver a therapeutically effective amount of the first lipophilic agent to a desired area in a subject.

An object of embodiments of the invention is to provide increased uptake of a drug into the vessel wall with minimal loss of the drug to the more hydrophilic systemic circulation.

A further object of embodiments of the invention is to provide a drug delivery system that reduces restenosis in percutaneous intervention of coronary arteries.

Other objects of the invention provide a better understanding of the in vivo pharmacokinetics of drug-eluting medical devices (including DES—drug-eluting stents).

Yet other object of embodiments of the invention is to provide a more highly lipophilic compound than rapamycin.

Still yet other objects of embodiments of the invention are to improve drug transport into tissue cells of the arterial wall and improve tissue retention of the drug.

Yet another object of embodiments of the invention is to provide a deeper penetration and wider distribution of the drug from the medical device to the adjacent tissue allowing therapeutically effect amounts of the drug to the targeted area in a subject.

It is to be understood that the foregoing general description and the following detailed description are exemplary and explanatory only and are not to be viewed as being restrictive of the invention as claimed. Further advantages of this invention will be apparent after a review of the following detailed description of the disclosed embodiments which are illustrated schematically in the accompanying drawings and in the appended claims.

DETAILED DESCRIPTION OF EMBODIMENTS OF THE INVENTION

Figure 1:
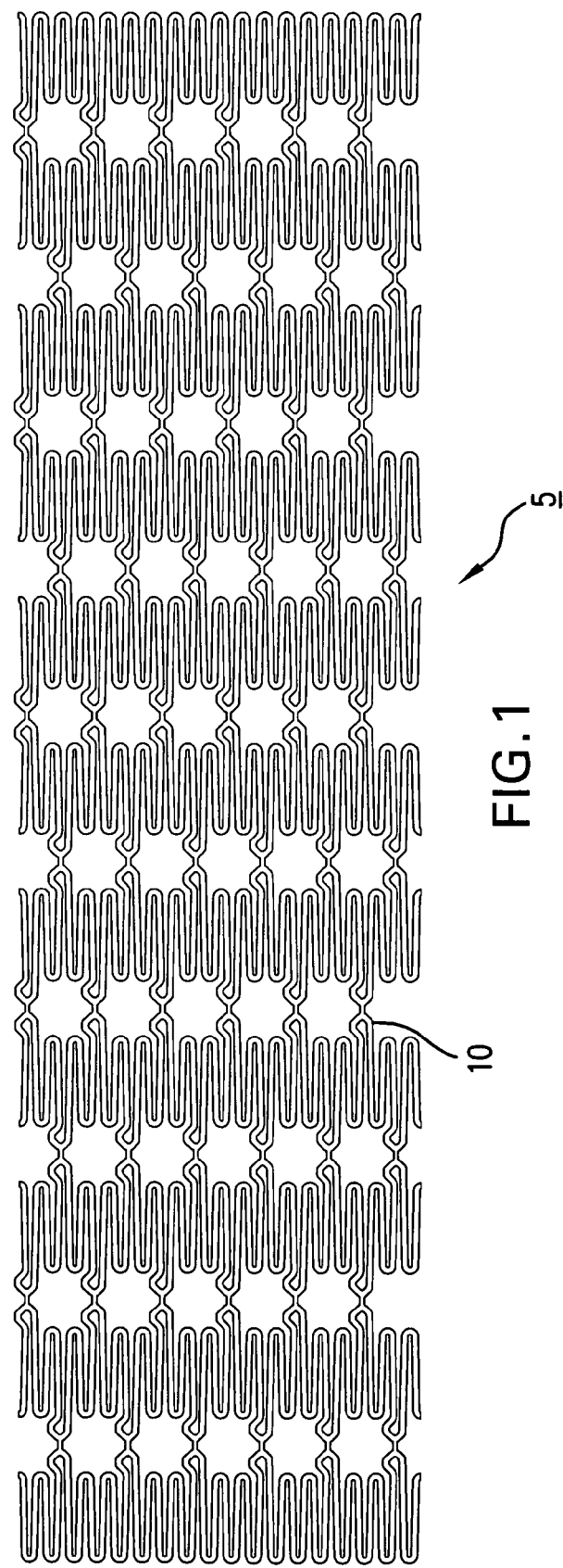
FIG. 1 is a side view of an exemplary interventional device (stent), according to embodiments of the invention.
Figure 2:
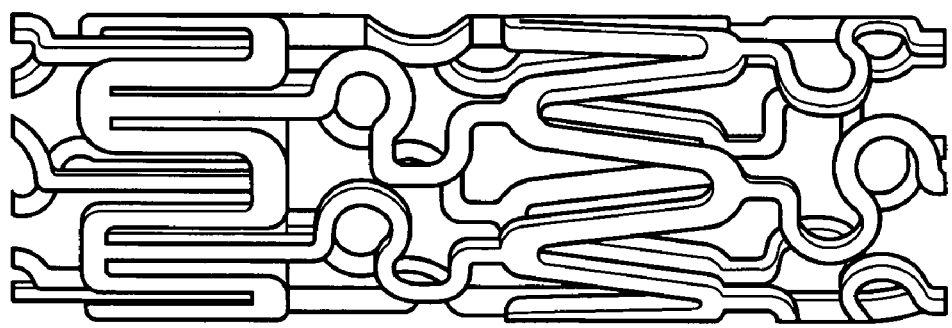
FIG. 2 is a side view in elevation showing a PC-coated (phosphorylcholine-coated) stent suitable for use in this invention, according to embodiments of the invention.
Figures 3A, 3B:
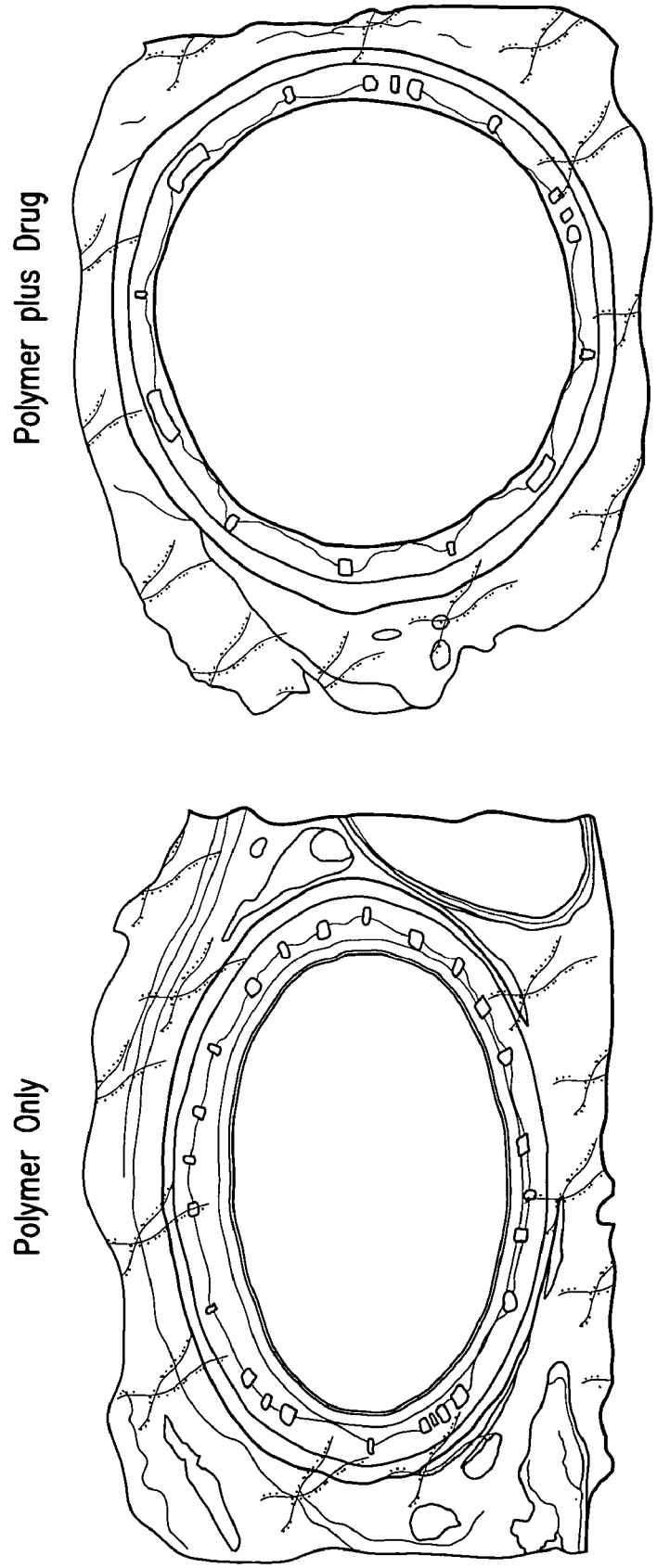
FIG. 3A is a cross-sectional view of a vessel segment in which was placed a stent coated with a polymer only, according to embodiments of the invention.
FIG. 3B is a cross-sectional view of a vessel segment in which was placed a stent coated with a polymer plus drug, according to embodiments of the invention.
Figure 4:
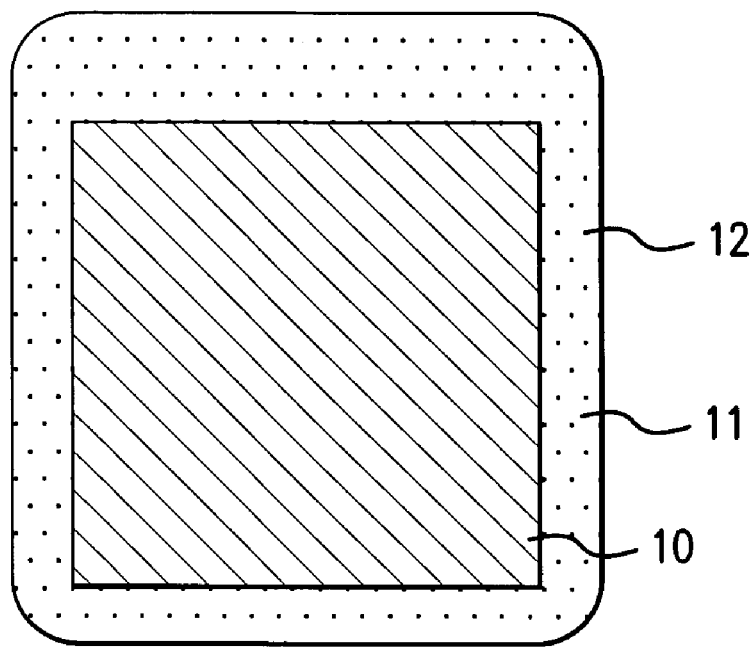
FIG. 4 is a cross-sectional view of a stent strut having a layer of a beneficial agent and hydration inhibitor in mixture, according to embodiments of the invention.

The invention relates to apparatuses, methods, and drug delivery systems for delivering a lipophilic agent to a body lumen. One aspect of the invention relates to a system for delivering a lipophilic agent including: a medical device, a first lipophilic agent capable of penetrating a body lumen, wherein the transfer coefficient of the first lipophilic agent is by an amount of at least approximately 5,000 (ug/mL)$^{-1}$, wherein the first lipophilic agent is associated with the medical device, wherein the first lipophilic agent/medical device is placed adjacent to said body lumen, and wherein a therapeutically effective amount of the first lipophilic agent is delivered to a desired area within a subject.

Another aspect of the invention relates to a method for improving patency in a subject involving placement of a medical device in a body lumen for treating and/or preventing adjacent diseases or maintaining patency of the body lumen including: providing a medical device in a body lumen, providing a first lipophilic agent capable of penetrating a body lumen, wherein the transfer coefficient of the first lipophilic agent is by an amount of at least approximately 5,000 (ug/mL)$^{-1}$, wherein the first lipophilic agent is associated with the medical device, placing the first lipophilic agent/medical device adjacent to a body lumen, and delivering a therapeutically effective amount of the first lipophilic agent to a desired area within a subject.

Yet another aspect of the invention relates to a medical device including: a therapeutically effective amount of a first lipophilic agent associated with the medical device, wherein the first lipophilic agent is capable of penetrating a body lumen, wherein the transfer coefficient of the first lipophilic agent is by an amount of at least approximately 5,000 (ug/mL)$^{-1}$, and wherein the first lipophilic agent/medical device is capable of being placed adjacent to a body lumen of a subject and deliver a therapeutically effective amount of the first lipophilic agent to a desired area in a subject.

Still yet another aspect of the invention relates to a stent including: a therapeutically effective amount of a first lipophilic agent associated with the stent, wherein the first lipophilic agent is capable of penetrating a body lumen, wherein the transfer coefficient of the first lipophilic agent is by an amount of at least approximately 5,000 (ug/mL)$^{-1}$, and wherein the first lipophilic agent/stent is capable of being placed adjacent to a body lumen of a subject and deliver a therapeutically effective amount of the first lipophilic agent to a desired area in a subject.

Definitions

It is noted that, as used in this specification and the appended claims, the singular forms "a," "an," and "the" include plural referents unless expressly and unequivocally limited to one referent. The term "agent" as used herein is synonymous with "at least one agent," "compound," or "at least one compound," and means at least one drug or codrug, or a prodrug thereof.

The term "beneficial agent," used herein, means agents that exert a therapeutically beneficial effect when delivered from suitable medical devices. "Beneficial agent" as used herein, refers to any compound, mixture of compounds, or composition of matter consisting of a compound, which produces a beneficial or useful result. The beneficial agent can be a polymer, a marker, such as a radiopaque dye or particles, or can be a drug, including pharmaceutical and therapeutic agents, or an agent including inorganic or organic drugs without limitation. The agent or drug can be in various forms such as uncharged molecules, components of molecular complexes, pharmacologically-acceptable salts such as hydrochloride, hydrobromide, sulfate, laurate, palmitate, phosphate, nitrate, borate, acetate, maleate, tartrate, oleate, and salicylate.

An agent or drug that is water insoluble can be used in a form that is a water-soluble derivative thereof to effectively serve as a solute, and on its release from the device, is converted by enzymes, hydrolyzed by body pH, or metabolic processes to a biologically active form. Additionally, the agents or drug formulations can have various known forms such as solutions, dispersions, pastes, particles, granules, emulsions, suspensions and powders. The drug or agent may or may not be mixed with polymer or a solvent as desired.

For purposes of illustration and not limitation, the drug or agent can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors. Other drugs or agents include but are not limited to antineoplastics, antimitotics, antifibrins, antioxidants, agents that promote endothelial cell recovery, antiallergic substances, radiopaque agents, viral vectors, antisense compounds, oligionucleotides, cell permeation enhancers, cell adhesion promoters, nucleic acids, monoclonal antibodies, hypogylcemic agents, hypolipidemic agents, proteins, agents useful for erythropoiesis stimulation, angiogenesis agents, and combinations thereof.

Examples of such antithrombotics, anticoagulants, antiplatelet agents, and thrombolytics include sodium heparin, low molecular weight heparins, heparinoids, hirudin, argatroban, forskolin, vapriprost, prostacyclin and prostacylin analogues, dextran, D-phe-pro-arg-chloromethylketone (synthetic antithrombin), dipyridamole, glycoprotein IIb/IIIa (platelet membrane receptor antagonist antibody), recombinant hirudin, and thrombin inhibitors such as Angiomax™, from Biogen, Inc., Cambridge, Mass.; and thrombolytic agents, such as urokinase, e.g., Abbokinase™ from Abbott Laboratories Inc., North Chicago, Ill., recombinant urokinase and pro-urokinase from Abbott Laboratories Inc., tissue plasminogen activator (Alteplase™ from Genentech, South San Francisco, Calif. and tenecteplase (TNK-tPA).

Examples of such cytostatic or antiproliferative agents include rapamycin and its analogs including everolimus, zotarolimus, i.e., 3S,6R,7E,9R,10R,12R,14S,15E,17E,19E, 21S,23S,26R,27R,34aS)-9,10,12,13,14,21,22,23,24,25,26, 27,32,33,34,34a-Hexadecahydro-9,27-dihydroxy-3-[(1R)-2-[(1S,3R,4R)-3-methoxy-4-tetrazol-1-yl)cyclohexyl]-1-methylethyl]-10,21-dimethoxy-6,8,12,14,20,26-hexamethyl-23,27-epoxy-3H-pyrido[2,1-c][1,4] oxaazacyclohentriacontine-1,5,11,28,29(4H,6H,31H)-pentone;23,27-Epoxy-3H pyrido[2,1-c][1,4] oxaazacyclohentriacontine-1,5,11,28,29(4H,6H,31H)-pentone, tacrolimus and pimecrolimus, angiopeptin, angiotensin converting enzyme inhibitors such as captopril, e.g, Capoten® and Capozide® from Bristol-Myers Squibb Co., Stamford, Conn., cilazapril or lisinopril, e.g., Prinivil® and Prinzide® from Merck & Co., Inc., Whitehouse Station, N.J.; calcium channel blockers such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, e.g. Mevacor® from Merck & Co., Inc., Whitehouse Station, N.J. In addition, topoisomerase inhibitors such as etoposide and topotecan, as well as antiestrogens such as tamoxifen may be used.

Examples of such anti-inflammatories include colchicine and glucocorticoids such as betamethasone, cortisone, dexamethasone, budesonide, prednisolone, methylprednisolone and hydrocortisone. Non-steroidal anti-inflammatory agents include flurbiprofen, ibuprofen, ketoprofen, fenoprofen, naproxen, diclofenac, diflunisal, acetominophen, indomethacin, sulindac, etodolac, diclofenac, ketorolac, meclofenamic acid, piroxicam and phenylbutazone.

Examples of such antineoplastics include alkylating agents including altretamine, bendamucine, carboplatin, carmustine, cisplatin, cyclophosphamide, fotemustine, ifosfamide, lomustine, nimustine, prednimustine, and treosulfin, antimitotics including vincristine, vinblastine, paclitaxel, e.g., TAXOL™ by Bristol-Myers Squibb Co., Stamford, Conn., docetaxel, e.g., Taxotere® from Aventis S.A., Frankfort, Germany, antimetabolites including methotrexate, mercaptopurine, pentostatin, trimetrexate, gemcitabine, azathioprine, and fluorouracil, and antibiotics such as doxorubicin hydrochloride, e.g., Adriamycin® from Pharmacia & Upjohn, Peapack, N.J., and mitomycin, e.g., Mutamycin® from Bristol-Myers Squibb Co., Stamford, Conn., agents that promote endothelial cell recovery including Estradiol.

Additional drugs which may be utilized in this application include inhibitors of tyrosine kinase such as RPR-101511A, PPAR-alpha agonists such as Tricor™ (fenofibrate) from Abbott Laboratories Inc., North Chicago, Ill., endothelin receptor antagonists including astrasentan (ABT-627) having general formula $C_{29}H_{38}N_2O_6 \cdot ClH$, and the following structural formula

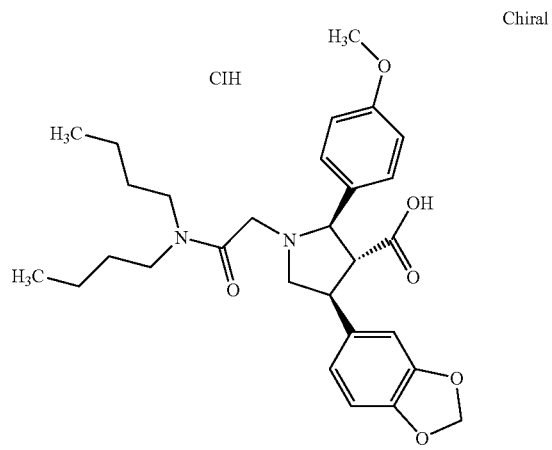

from Abbott Laboratories Inc., North Chicago, Ill.; matrix metalloproteinase inhibitors such as ABT-518 having general formula $C_{21}H_{22}F_3NO_8S$ and having the following structural formula

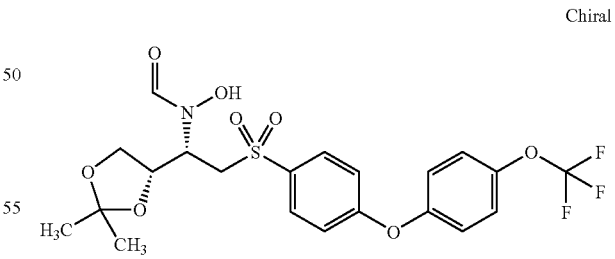

from Abbott Laboratories Inc., North Chicago, Ill., antiallergic agents such as permirolast potassium nitroprusside, phosphodiesterase inhibitors, prostaglandin inhibitors, suramin, serotonin blockers, steroids, thioprotease inhibitors, triazolopyrimidine, and nitric oxide.

When at least one beneficial agent is utilized in the invention, the beneficial agent includes, but is not limited to, at least one of antiulcer/antireflux agents, and antinauseants/antiemetics, and any combinations thereof. When at least one beneficial agent is utilized in the invention, the beneficial agent includes, but is not limited to, at least one of phenyl salicylate, β-estradiol, testosterone, progesterone, cyclosporin A, carvediol, vindesine, folic acid, thrombospondin mimetics, estradiol, metrizamide, iopamidol, iohexol, iopromide, iobitridol, iomeprol, iopentol, ioversol, ioxilan, iodixanol, iotrolan and pro-drugs, analogs, derivatives, and any combinations thereof.

While the above beneficial agents are known for their preventive and treatment properties, the substances or agents are provided by way of example and are not meant to be limiting. Further, other beneficial agents that are currently available or may be developed are equally applicable for use with embodiments of the invention.

The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction, in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible.

The term "preventing" is art-recognized, and when used in relation to a condition, including a local recurrence (e.g., pain), a disease including cancer, a syndrome complex including heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the beneficial agent. The polymer can be biocompatible, or biodegradable. For purpose of illustration and not limitation, the polymeric material include phosphorylcholine linked macromolecules, including a macromolecule containing pendant phosphorylcholine groups such as poly(MPC$_w$:LMA$_x$:HPMA$_y$:TSMA$_z$), where MPC is 2-methacryoyloxyethylphosphorylcholine, LMA is lauryl methacrylate, HPMA is hydroxypropyl methacrylate and TSMA is trimethoxysilylpropyl methacrylate, polycaprolactone, poly-D,L-lactic acid, poly-L-lactic acid, poly(lactide-co-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, Parylene.RTM., Parylast.RTM., polyurethane including polycarbonate urethanes, polyethylene, polyethylene terapthalate, ethylene vinyl acetate, ethylene vinyl alcohol, silicone including polysiloxanes and substituted polysiloxanes, polyethylene oxide, polybutylene terepthalate-co-PEG, PCL-co-PEG, PLA-co-PEG, polyacrylates, polyvinyl pyrrolidone, polyacrylamide, and combinations thereof. Non-limiting examples of other suitable polymers include thermoplastic elastomers in general, polyolefin elastomers, EPDM rubbers and polyamide elastomers, and biostable plastic material including acrylic polymers, and its derivatives, nylon, polyesters and expoxies. Other polymers include pendant phosphoryl groups as disclosed in U.S. Pat. Nos. 5,705,583 and 6,090,901 to Bowers et al. and U.S. Pat. No. 6,083,257 to Taylor et al., and U.S. Pat. Nos. 5,705,583 and 6,090,901 teach phosphorylcholine polymers (including PC-1036 and PC-2126), which are all incorporated herein by reference.

The term "pro-drug," as used herein, refers to compounds, which are transformed in vivo to the parent compound of the formula above, for example, by hydrolysis in blood. A thorough discussion is provided by T. Higuchi and V. Stella, "Pro-drugs as Novel Delivery systems," Vol. 14 of the A.C.S. symposium Series, and in Edward B. Roche, ed., "Bioreversible Carriers in Drug Design." American Pharmaceutical Association and Pergamon Press, 1987, both of which are incorporated herein by reference.

The term "subject" as used herein, refers to any warm-blooded animal and mammals including, but not limited to, humans, pigs, dogs, monkeys, cows, goats, sheep, horses, rats, mice, and guinea pigs.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The following are working and prophetic examples of embodiments of the above aspects and are by no means limiting. Zotarolimus (ABT-578), rapamycin, siroilums (rapamycin), biolimus A-9, everolimus, paclitaxel, dexamethasone, and estradiol are all being proposed for use in drug-eluting stents to reduce restenosis in percutaneous intervention of coronary arteries. Since local drug delivery and tissue uptake are a function of drug solubility and lipophilicity, a study was conducted to determine the precise physicochemical profile for these compounds. Solubilities of the drug molecules (both crystalline and amorphous forms) and lipophilicity (LogP), were determined. The results of these studies provide a better understanding of the in vivo pharmacokinetics of drug-eluting stents.

Methods of Determining Solubility and Partition Coefficients of Various Drugs

"Solubility" is based on a standard measure used in medicinal chemistry. The octanol-water partition coefficient (P) is the ratio of distribution of a compound in a mixture of 1-octanol and $H_2O$. LogP is the base 10 logarithm of the partition coefficient.

$$P = \frac{C(n-\text{octanol})}{C(\text{water})}$$

Compounds with LogP values greater than about 1 are considered lipophilic (greater solubility in 1-octanol versus $H_2O$). One can use a variety of computerized protocols to perform calculated estimates of the LogP value. One such computer program is ChemDraw Pro Version 5.0 from CambridgeSoftCorporation. To calculate the LogP coefficient one can use the Crippen's fragmentation method (Crippen et. al., J. Chem. Inf. Comput. Sci. 1987, 27, 21).

The shake-flask method was used in both the solubility and partition coefficient studies. Preliminary analyses were conducted to evaluate the optimum conditions for both methods. For the partition coefficient methodology, drug was dissolved in an organic phase (n-octanol), followed by the addition of buffered water to extract the drug from the organic phase. Ultimately, the drug concentrations in both phases reach an equilibrium determined by the partition coefficient of the drug compound. For solubility testing, an initial evaluation was conducted to ensure full separation of drug particles from the saturated solution, and to avoid adsorption of drug by the experimental apparatus. The measurements were performed at multiple equilibration times (from 2 hours up to 5 days). Concentrations of all drug compounds were assayed by validated HPLC methods.

In the measurement of the partition coefficient (octanol/water), preliminary studies were conducted to determine the optimum drug concentration for each test, and the appropriate time for establishing the partition equilibrium. All experiments were carried out by two different analysts and on multiple drug lots.

Figure 20:
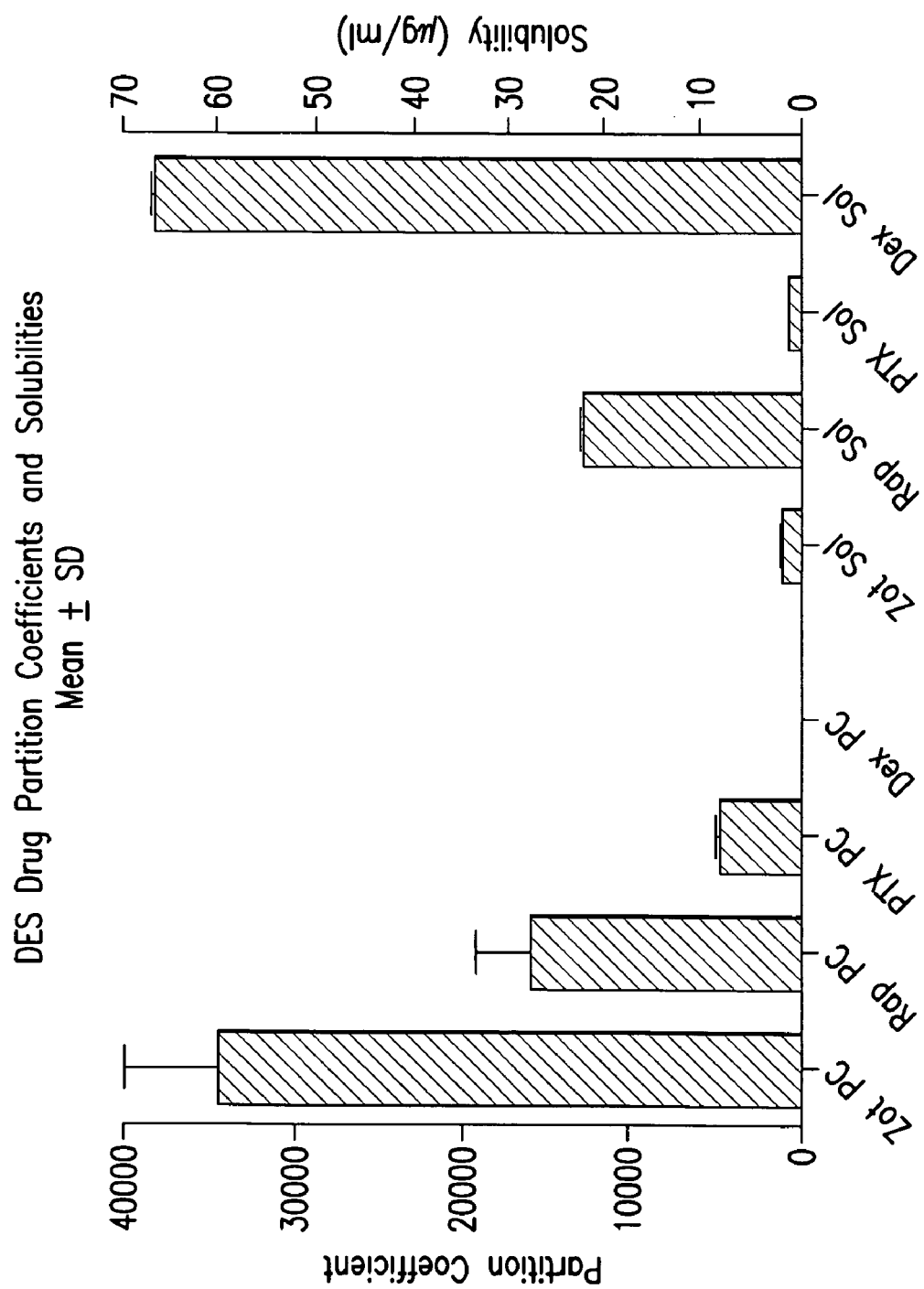
FIG. 20 is a graph illustrating the partition coefficients and solubilities of various drugs utilized in drug-eluting devices, according to embodiments of the invention.

Results are shown in the FIG. 20 (DES=drug-eluting stents). Partition coefficients vary by over a factor of 400 between drugs. The results indicated that the "limus" drugs zotarolimus and rapamycin are the most lipophilic compounds in the group tested. Of these, zotarolimus is more than two times as lipophilic as rapamycin. The results of these experiments indicate that zotarolimus, a rapamycin analog in current clinical trials for delivery from the ZoMaxx™ coronary drug-eluting stent (Abbott Vascular Inc.) is much less soluble in water than amorphous rapamycin, and is the most lipophilic of all DES drugs tested. This characteristic suggests preferential uptake of zotarolimus into the vessel wall, with minimal loss of the drug to the more hydrophilic systemic circulation. Lipophilicity improves drug transport into tissue cells of the arterial wall and improves tissue retention of the drug.

Drug delivery in DES ideally occurs with predominate tissue uptake, however, drug also partitions into the blood. Consequently, high aqueous solubility may have a negative impact on local drug bioavailability. It has been determined by the above tests that lipophilicity and solubility are controlling factors in DES drug delivery.

While most drug-eluting stents have amorphous drugs mixed in a polymer matrix, the bulk DES drug exists in either amorphous or crystalline forms. Therefore, solubility data on DES drugs was investigated for both the amorphous and crystalline forms. It was found that rapamycin can be either amorphous or crystalline, zotarolimus is amorphous, and paclitaxel has two crystal forms. Aqueous solubility of amorphous DES drugs follow the increasing order: paclitaxel, zotarolimus, rapamycin, and dexamethasone (crystalline).

Figure 21:
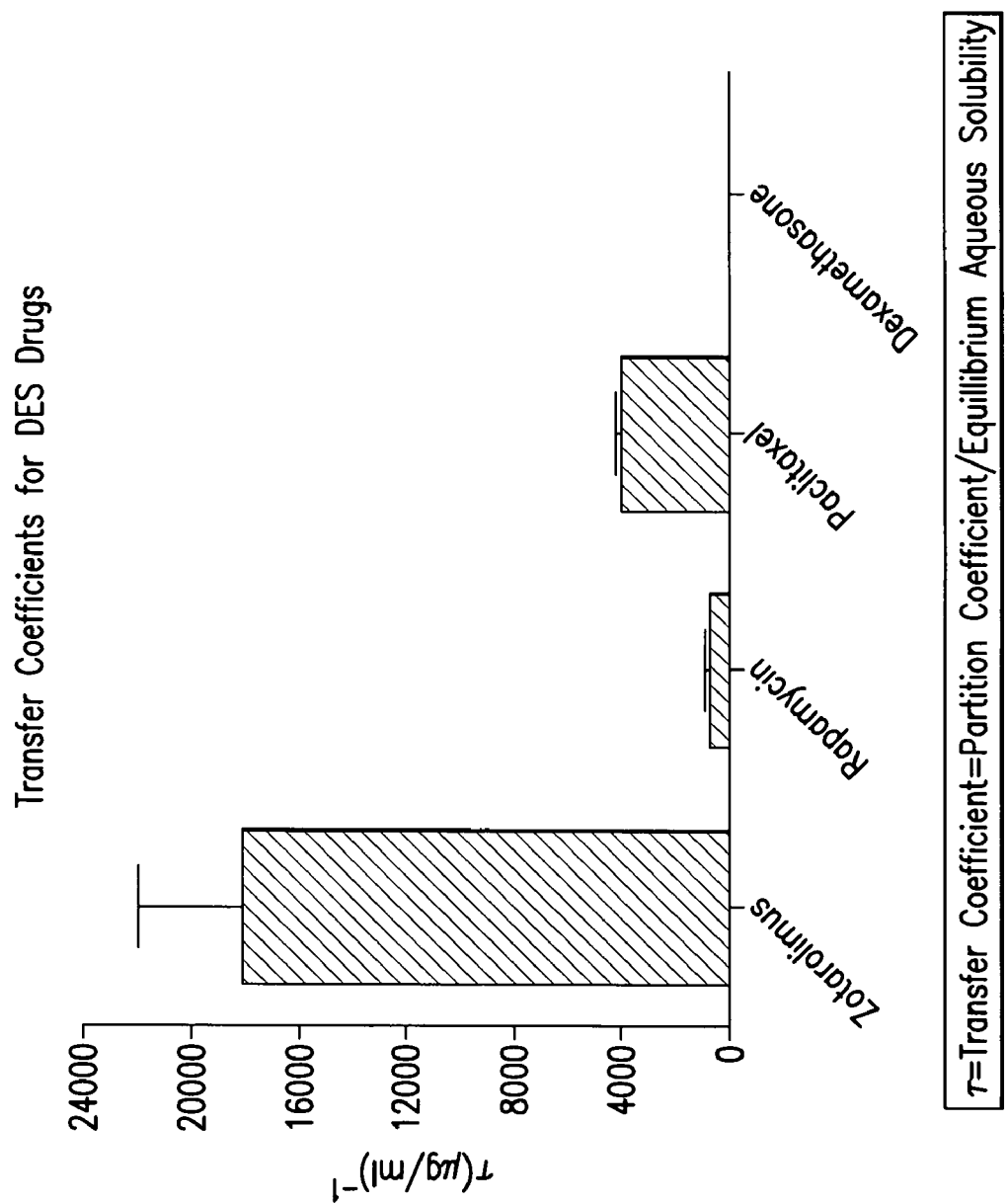
FIG. 21 is a graph illustrating the transfer coefficients for various drugs utilized in drug-eluting devices, according to embodiments of the invention.

A transfer coefficient, T, can be defined as P divided by S, where P equals the partition coefficient and S equals the equilibrium aqueous solubility, (µg/ml) as shown in FIG. 21. These studies demonstration that the transfer coefficient for the DES drug studied are in the order zotarolimus>>paclitaxel>>rapamycin>dexamethasone.
Where S equals the equilibrium aqueous solubility of the amorphous form of the drug were possible.

The aspects of the invention further include at least one pharmaceutically acceptable carrier or excipient, wherein the medical device is associated with the pharmaceutically acceptable carrier or excipient. In embodiments, the pharmaceutically acceptable carrier or excipient is a polymer. In other embodiments, the pharmaceutically acceptable carrier or excipient is an agent. When a polymer is utilized as the pharmaceutically acceptable carrier or excipient, the delivery mechanism of the first lipophilic agent includes polymer hydration followed by dissolution of the first lipophilic agent, and wherein the first lipophilic agent is thereafter delivered into the body lumen. Another delivery mechanism includes the first lipophilic agent/polymer matrix controlling the elution rate of the first lipophilic agent to the body lumen.

Embodiments of the invention further include at least one of the following: at least one second lipophilic agent, at least one lipophilic prodrug, at least one beneficial agent, at least one lipophilic penetration enhancer, and any combination thereof. In embodiments when a lipophilic penetration enhancer is utilized, the enhancer is a pharmaceutical agent.

A further embodiment of the invention is to provide drug delivery to the myocardial wall to reduce the area or extent of ischemic or infarcted cardiac tissue. Examples of agents to be used for this purpose include, but are not limited to, calcium channel blockers (nifedipine, diltiazem, nicardipine and verapamil), beta-adrenergic blocking agents (nadolol, metoprolol, propranolol, atenolol and esmolol) and nitrates (nitroglycerin and isosorbide dinitrate). Yet another embodiment of the invention is to deliver drug to hypokinetic or akinetic regions of the myocardial wall to improve contractility of the cardiac muscle in the treatment of heart failure. Drug examples include, but are not limited to carvedilol, an adrenergic antagonist with nonselective beta- and a1-receptor blocking properties, cardiac glycosides such as digitalis, and calcium sensitizers such as levosimendan. Delivery of agents to stabilize vulnerable plaque, such as inhibitors of matrix metalloproteinases (batimistat, prinomastat, marimistat and ABT-518) or the macrolide antibiotic azithromycin, may also be delivered. To maintain patency of body lumens including, but not limited to, the urethra, the delivery of chemotherapeutic agents such as alkylating agents and antimetabolites may be utilized.

The concentration of the first lipophilic agent delivered into the body lumen or desired targeted area is a therapeutically effective amount. When a second lipophilic agent is utilized, the concentration of the second lipophilic agent in combination with the first lipophilic agent is delivered into the body lumen or desired targeted area in a therapeutically effective amount.

When utilized in the invention, the first lipophilic agent and/or second lipophilic agent zotarolimus having the structures as follows.

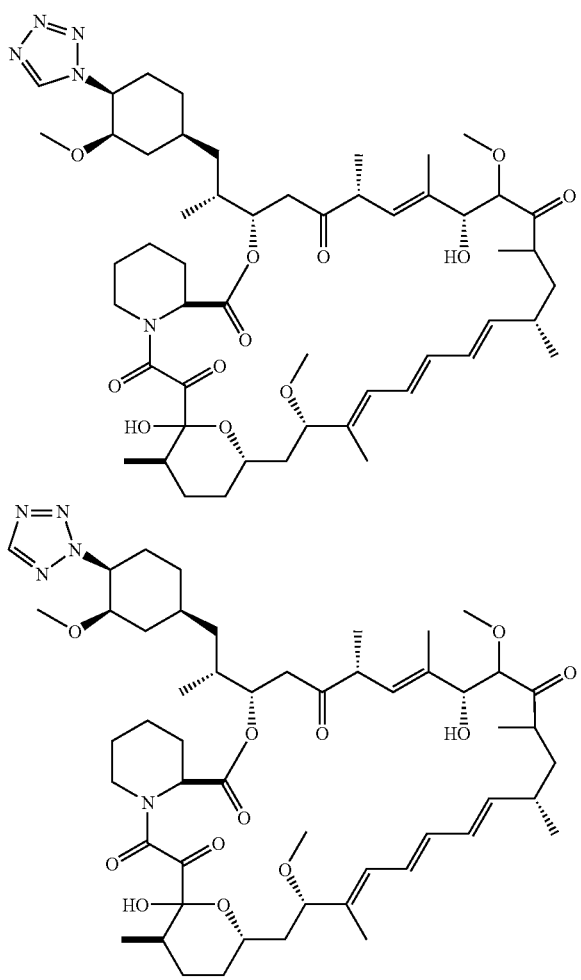

The body lumen in the application includes, but is not limited to, a vessel wall, either arterial or venous. In other embodiments, the body lumen includes, but is not limited to, at least one of a vessel wall, a coronary artery, esophageal lumen, or a urethra. For example, such as, the first lipophilic agent/medical device is placed adjacent to a body lumen (coronary arteries) and a therapeutically effective amount of the first lipophilic agent is delivered into said coronary arteries and is diffused into the pericardial sac in a drug delivery system. In embodiments, the invention provides for substantially uniform dug delivery of the lipophilic agent to the myocardium and/or is useful for the treatment and/or prevention of vascular diseases in a subject. In embodiments, the lipophilic agent is continuously delivered to the epicardium and/or pericardial sac.

Figure 24:
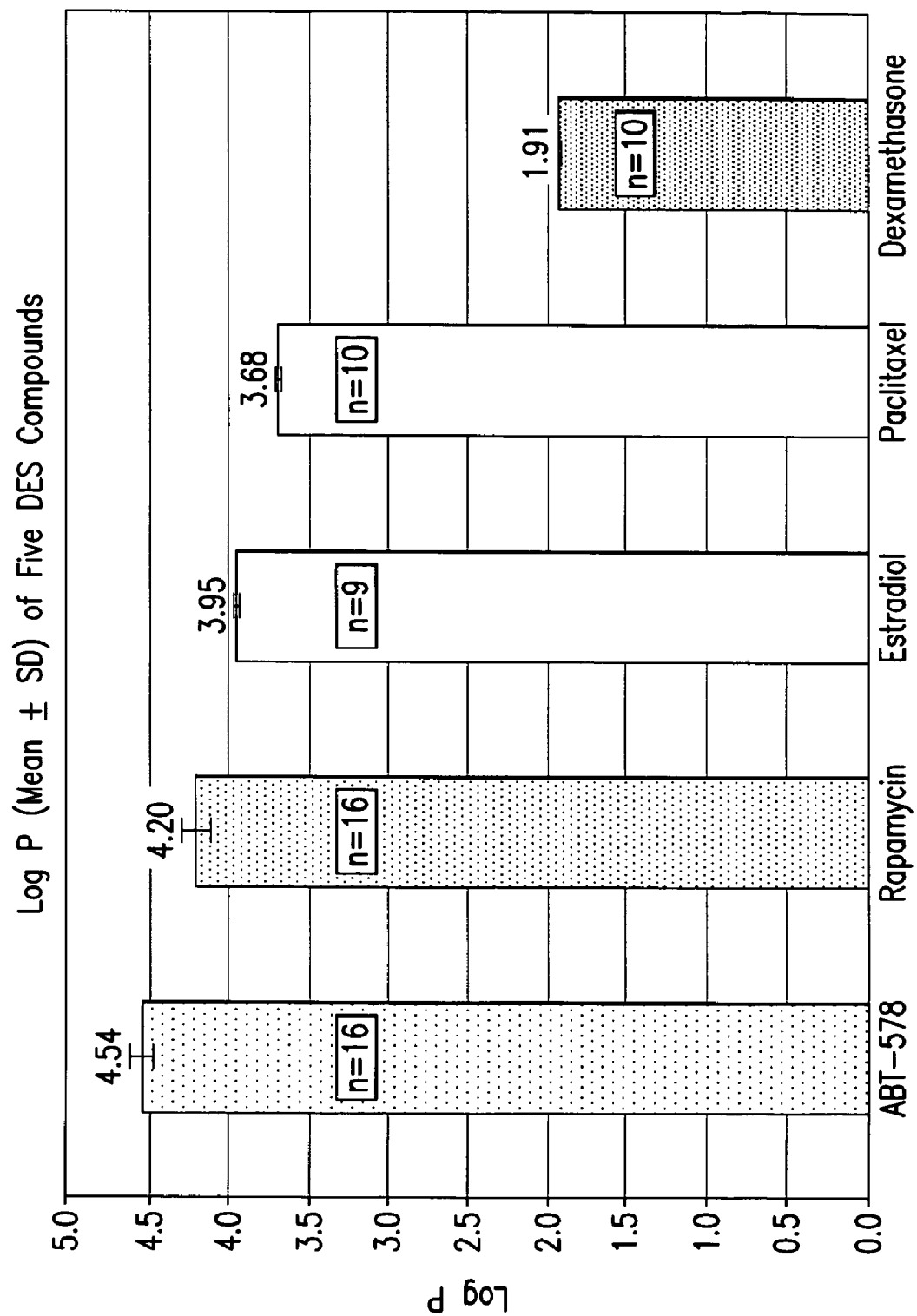
FIG. 24 is a graph illustrating the LogP values of various drug compounds, according to embodiments of the invention.

Embodiments of the first lipophilic agent includes agents with partition coefficients greater than 20,000. In embodiments of the invention, the first lipophilic agent includes transfer coefficients of at least approximately 10,000 $(\mu g/mL)^{-1}$. In other embodiments, the first lipophilic agent includes transfer coefficient of at least approximately 15,000 $(\mu g/mL)^{-1}$. Embodiments of the first lipophilic agent include compounds having LogP of at least approximately 4.3, as shown in FIG. 24. The first lipophilic agent includes partition coefficient greater than 20,000 P and the lipophilic agent includes a solubility of less than about 30 ug/ml. In embodiments, the first lipophilic agent is amorphous.

Figure 22:
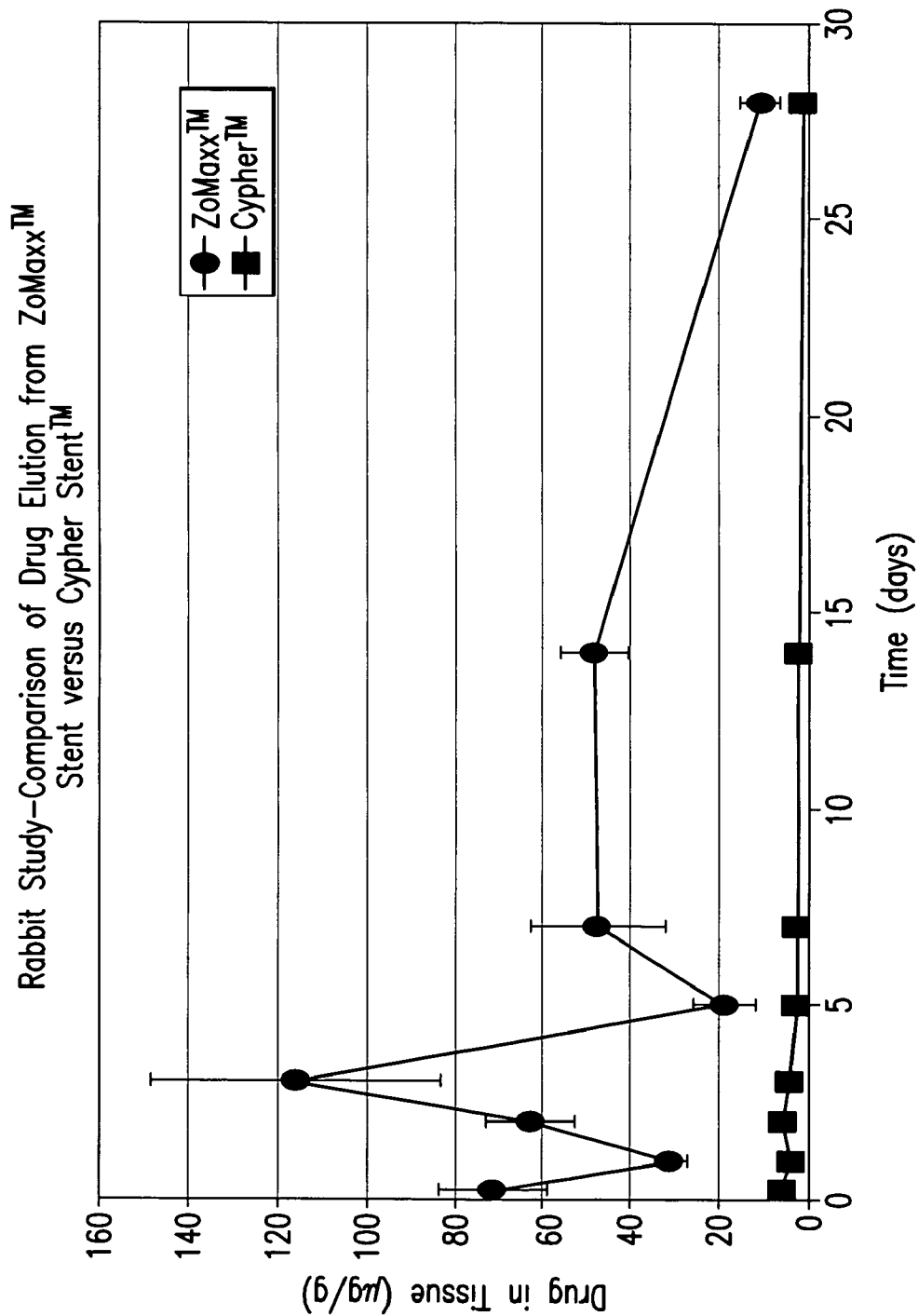
FIG. 22 is a graph illustrating the amount of drug concentration (ZoMaxx™ stent vs Cypher® stent) in rabbit tissue over 28 days, according to embodiments of the invention.

FIG. 22 is a rabbit study comparing the drug concentration in rabbit tissue by drug elution from the ZoMaxx™ stent vs. the Cypher® stent. The dosage delivery of the first lipophilic agent into the vascular tissue ranges from about 15 µg/g to about 150 µg/g over a period of up to about 5 days. In other embodiments, the dosage delivery of the first lipophilic agent into the vascular tissue ranges from about 15 µg/g to about 80 µg/g over a period from about 5 to up to about 15 days. At no time points between 0 and 15 days, the comparator Cypher® stent reaches concentrations of rapamycin higher than 10 µg/g. Still in other embodiments, the dosage delivery of the first lipophilic agent into the vascular tissue ranges from about 5 µg/g to about 60 µg/g over from 15 to up to about 28 days. Still in other embodiments, the dosage delivery of the first lipophilic agent is always greater than 5 times the dose delivery of the comparative Cypher® stent at the 28 day point.

Figure 23:
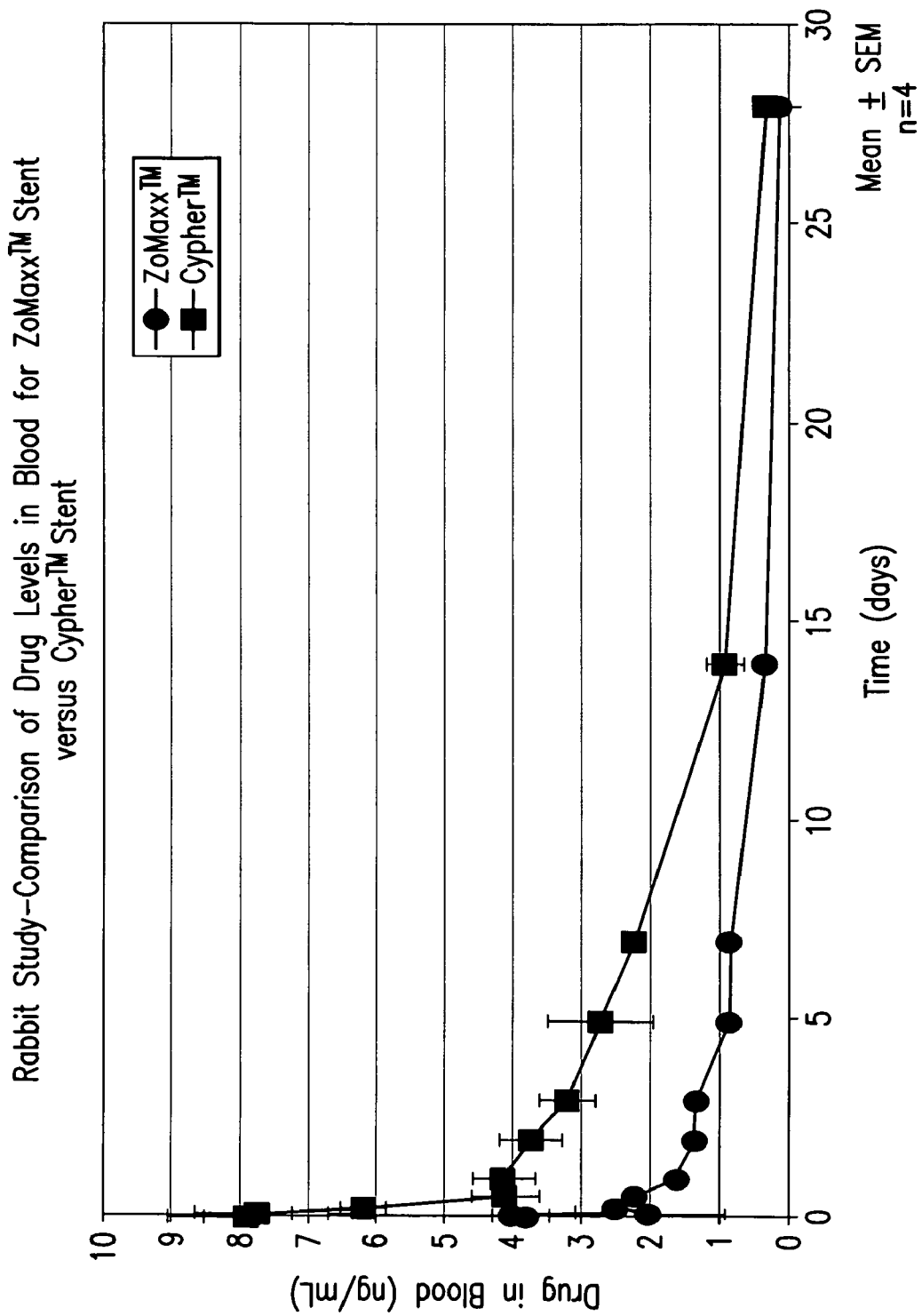
FIG. 23 is a graph illustrating the amount of drug concentration (ZoMaxx™ stent vs Cypher® stent) in rabbit blood over 28 days, according to embodiments of the invention.

FIG. 23 is a from the same rabbit study comparing the drug levels in rabbit blood for ZoMaxx™ stent vs. Cypher® stent. The blood levels of rapamycin eluted from the Cypher® stents are consistently significantly higher than the blood levels of zotarolimus eluted from the ZoMaxx™ stents.

Figure 25:
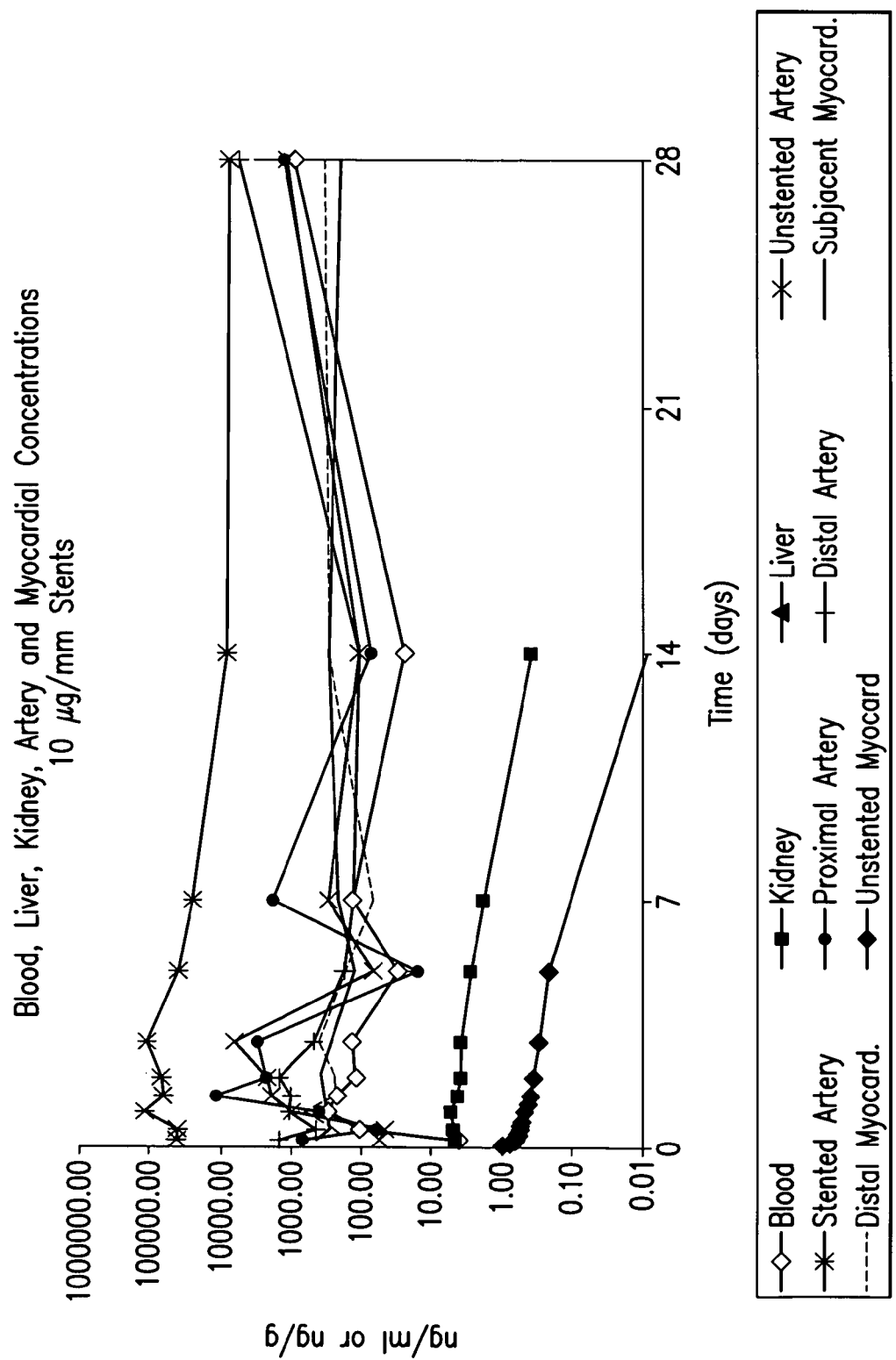
FIG. 25 is a graph illustrating the results of experiments performed in pigs utilizing zotarolimus, graph shows the blood, liver, kidney, artery, and myocardial concentrations of zotarolimus, according to embodiments of the invention.

FIG. 25 is a graph demonstrating blood, liver, kidney, artery and myocardial concentrations of zotarolimus eluted from ZoMaxx™ tents in a pig model Zotarolimus is delivered in substantial concentrations to the arterial tissue adjacent to the stent placement at all periods out to 28 days. Unexpectedly, zotarolimus also reaches therapeutically significant concentrations in the distal myocardium, the unstent myocardium, and in the subjacent myocardium and in unstented and distal coronary arteries and maintains those concentrations throughout the 28 day course of the experiment.

In embodiments of the invention, the medical device includes, but is not limited to, an endovascular medical device. In embodiments, the medical device includes intracoronary medical devices including at least one of stents, drug delivery catheters, grafts, and drug delivery balloons utilized in a subjects' vasculature. When the medical device is a stent, the stent includes peripheral stents, peripheral coronary stents, degradable coronary stents, non-degradable coronary stents, self-expanding stents, balloon-expanded stents, and esophageal stents. In other embodiments, the medical device includes at least one of, but is not limited to, arterio-venous grafts, by-pass grafts, penile implants, vascular implants and grafts, intravenous catheters, small diameter grafts, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

Yet in other embodiments, the medical device includes at least one of, but is not limited to, either arterial or venous, pacemakers, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue adhesives, tissue sealants, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuro aneurysm treatment coils, hemodialysis devices, uterine bleeding patches, anastomotic closures, in vitro diagnostics, aneurysm exclusion devices, neuropatches, vena cava filters, urinary dilators, endoscopic surgical and wound drainings, surgical tissue extractors, transition sheaths and dialators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, drug delivery capsule and cardiac valves. For example, such as, the first lipophilic agent/medical device is placed adjacent to a body lumen (arteries, veins or grafts) and a therapeutically effective amount of the first lipophilic agent is delivered into said arteries, veins or grafts and is diffused into the pericardial sac in a drug delivery system. In embodiments, the invention provides for substantially uniform dug delivery of the lipophilic agent to the myocardium and/or is useful for the treatment and/or prevention of vascular diseases in a subject. The medical device is permanently or temporarily implanted into a subject.

In accordance with the invention, a medical device is provided having an interventional component that is loaded with a beneficial agent that is associated with a hydration inhibitor to control the delivery of the beneficial agent in a patient. As used herein "medical device" refers broadly to any device that is deployed in a patient. In an embodiment, the invention is directed to a medical device having controlled delivery of a beneficial agent for the treatment and prevention of cardio, vascular or other intraluminal diseases. The medical device is suitable for intraluminal delivery or implantation.

As is known in the art, such devices can comprise one or more interventional components. For purposes of illustration and not limitation, examples of such medical devices include stents, grafts, stent-grafts, valves, filters, coils, staples, sutures, guidewires, catheters, catheter balloons, and the like. In an embodiment, the interventional component is an interventional component having a first cross-sectional dimension for the purpose of delivery and a second cross-sectional dimension after deployment and can be deployed by known mechanical techniques including balloon expansion deployment techniques, or by electrical or thermal actuation, or self-expansion deployment techniques, as well known in the art. For example, and as embodied herein, representative embodiments of a stent, stent-graft or similar interventional component are disclosed in U.S. Pat. No. 4,733,665 to Palmaz; U.S. Pat. No. 6,106,548 to Roubin et al.; U.S. Pat. No. 4,580,568 to Gianturco; U.S. Pat. No. 5,755,771 to Penn et al.; and U.S. Pat. No. 6,033,434 to Borghi, are all incorporated herein by reference. It is recognized, however, that the interventional component can be any type of implantable or deployable interventional component capable of being loaded with beneficial agent.

The interventional component can be in an expanded or unexpanded state during the loading of beneficial agent. The underlying structure of the interventional component can be virtually any construction and the interventional component can be composed any suitable material including, but not limited to, stainless steel, "MP35N," "MP20N," elastinite (Nitinol), tantalum, nickel-titanium alloy, platinum-iridium alloy, chromium-cobalt alloy, gold, magnesium, polymer, ceramic, tissue, or combinations thereof. "MP35N" and "MP20N" are understood to be trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium and 10% molybdenum. Similarly, the interventional component can be made from bioabsorbable or biostable polymers. In some embodiments, the surface of the interventional component is porous or impervious, or include one or more reservoirs or cavities formed therein for purpose of retaining beneficial agent therein as is known in the art.

The interventional component can be fabricated utilizing any number of methods known in the art. For example, the interventional component can be fabricated from a hollow or formed tube that is machined using lasers, electric discharge milling, chemical etching or other known techniques. Alternatively, the interventional component can be fabricated from a sheet or formed of a wire or filament construction as known in the art.

In accordance with the present invention, the interventional component is loaded with beneficial agent to be delivered therefrom when deployed within the patient. "Beneficial agent" as used herein, generally refers to any compound, mixture of compounds, or composition of matter consisting of a compound, which produces a beneficial or useful result in a patient. The beneficial agent has a first LogP value.

The symbol "P" of "LogP" is the calculated partition coefficient of a chemical substance, which is a measure of the way in which a compound will partition itself between the octanol and water phases in the two-phase octanol-water system, and thus an indicator of certain types of biological activity. Specifically, P is the ratio of the concentration (in moles per liter) of the compound in the octanol phase to that in the water phase at infinite dilution. The solubility is usually expressed as base 10 logarithm of the partition coefficient, LogP. LogP and methods for calculating it are well known to those skilled in the art. The LogP value can be calculated by the method described in (Hansch C. and Leo A. "Substituent Constants for Correlation Analysis in Chemistry and Biology" Wiley, N.Y., 1979). The characteristic of being "relatively less hydrophilic" or "relatively more hydrophilic" as disclosed herein is determined according to the LogP value calculations. A discussion of methods of measurement and accuracy considerations for LogP is found in Sangster, J., J. Phys. Chem. Ref. Data, 18, 1111, 1989, incorporated herein by reference. LogP values can also be calculated by the method described in Hansch C. and Leo A. "Substituent Constants for Correlation Analysis in Chemistry and Biology" Wiley, N.Y., 1979. Other discussions of LogP may be found in the following documents, incorporated herein by reference: Mackay, D., Shiu, W. Y., and Ma, K. C., Illustrated Handbook of Physical-Chemical Properties and Environmental Fate for Organic Chemicals, Lewis Publishers/CRC Press, Boca Raton, Fla., 1992; Shiu, W. Y., and Mackay, D., J. Phys. Chem. Ref. Data, 15, 911, 1986; Pinsuwan, S., Li, L., and Yalkowsky, S. H., J. Chem. Eng. Data, 40, 623, 1995; Solubility Data Series, International Union of Pure and Applied Chemistry, Vol. 20, Pergamon Press, Oxford, 1985; Solubility Data Series, International Union of Pure and Applied Chemistry, Vol. 38, Pergamon Press, Oxford, 1985; Miller, M. M., Ghodbane, S., Wasik, S. P., Tewari, Y. B., and Martire, D. E., J. Chem. Eng. Data, 29, 184, 1984.

LogP is a widely used parameter for correlating biological effects of organic substances. It is a property of the two-phase system in which water and 1-octanol are in equilibrium at a fixed temperature and the substance is distributed between the water-rich and octanol-rich phases.

Generally, the greater the LogP value of a compound or agent, the less hydrophilic the compound or agent. It also has been determined that a compound or agent having a greater LogP value (i.e., a "relatively less hydrophilic agent") will inhibit hydration of the second compound or agent having a lower LogP value (i.e., a "relatively more hydrophilic agent"). Thus, and in accordance with embodiments of the invention, a relatively less hydrophilic agent can be used as a hydration inhibitor for a relatively more hydrophilic beneficial agent, which is to be delivered from an interventional component as a beneficial agent, wherein the hydration inhibitor has a LogP value that is greater than the LogP value of the beneficial agent. In embodiments, the LogP value of the hydration inhibitor is at least 0.1 units greater than the beneficial agent and at least 0.5 units greater than the beneficial agent. Particularly, and in an embodiment of the invention, the LogP value of the beneficial agent is less than 4.5 units, and more preferably it is less than 3.0 units. See "CRC Handbook of Chemistry and Physics," 3rd Electronic Edition, 2000. However, it is possible for a compound to serve as a hydration inhibitor of the elution of a given beneficial agent according to embodiments of the invention when the beneficial agent's LogP value is less than that of the given hydration inhibitor. Although those skilled in the art are familiar with LogP values and the well-known methods for calculation thereof, for purpose of illustration, and not limitation, Table 1 provides a representative summary of LogP values for several suitable beneficial agents for use with embodiments of the invention.

TABLE 1

| Beneficial Agent | LogP Values |
| --- | --- |
| Probucol | >8 |
| Linolenic acid | >6 |
| Linoleic acid | >6 |
| Stearic acid | >6 |
| Oleic acid | >6 |
| Paclitaxel | >5 |
| Danazol | 4.5 |
| Rapamycin | >4.5 |
| Zotarolimus | >4.5 |
| Tacrolimus | >4.5 |
| Fenofibrate | >4.5 |
| Indomethacin | 4.3 |
| Phenyl salicylate | 4.1 |
| B-estradiol | 4 |
| Vinblastine | 3.6 |
| ABT-627 | 3.4 |
| Testosterone | 3.3 |
| Progesterone | 3.2 |
| Paclitaxel | >3 |
| Cyclosporin A | 2.9 |
| Vincristine | 2.6 |
| Carvedilol | 1.97 |
| Dexamethasone | ~1.9-2.2 |
| Vindesine | 1.3 |
| Dipyridamole | 1-2 |
| Methotrexate | −1.85 |

A variety of suitable beneficial agents for delivery of an interventional component are well known. For example, and not limitation, various suitable beneficial agents having a LogP value include markers, such as, for example, a radiopaque dyes or particles, drugs, such as, for example, pharmaceutical and therapeutic agents, and inorganic or organic drugs without limitation. The agent or drug can be in various forms, components of molecular complexes, pharmacologically-acceptable salts such as hydrochloride, hydrobromide, sulfate, phosphate, nitrate, borate, acetate, maleate, tartrate and salicylate.

For purposes of illustration and not limitation, the drug or agent includes antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligionucleotides, cell permeation enhancers, pro-drugs and combinations thereof. Other beneficial agents include but are not limited to nucleic acids that encode a pharmaceutically useful peptide or an anti-sense oligo-nucleotide used to control a gene of interest in a cell.

Examples of specific beneficial agents of interest include indomethacin, phenyl salicylate, β-estradiol, vinblastine, ABT-627 (atrasentan), testosterone, progesterone, paclitaxel, cyclosporin A, vincristine, carvedilol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, iotrolan and pro-drugs, analogs, derivatives, or combinations thereof. Beneficial agents can have various art known forms including solutions, dispersions, pastes, particles, granules, emulsions, suspensions and powders. The beneficial agent typically is associated with the hydration inhibitor as a mixture, although can be associated as a separate application, including an overcoat or layer when a beneficial agent is used as the hydration inhibitor as disclosed further below.

While the foregoing beneficial agents are well known for their preventive and treatment properties, the substances or agents are provided by way of example and not limitation. Further, other beneficial agents with suitable LogP values that are currently available or can be developed are equally applicable for use with the invention.

Further in accordance with embodiments of the invention, an effective amount of hydration inhibitor is associated with the beneficial agent to be delivered from the interventional component so as to control delivery therefrom. The term "hydration inhibitor" as used herein refers to a suitable compound or agent or the like having a LogP value greater than that of the beneficial agent. The hydration inhibitor is thus relatively less hydrophilic than the beneficial agent, and controls delivery of the beneficial agent by retarding, inhibiting or otherwise sustaining the rate in which the beneficial agent would be delivered from the interventional component without the hydration inhibitor associated therewith. Delivery of the beneficial agent from the interventional component occurs by any of a variety of know mechanisms, including elution, diffusion, dissolution, permeation or other transport mechanisms in vivo.

Generally, "effective amount" of hydration inhibitor refers to an amount sufficient to inhibit hydration of the beneficial agent to be delivered from the interventional component. For example, it is well known to determine hydration as a measure of optical contact angle, wherein a contact angle of about 30° is indicative of a hydrophilic compound and a contact angle of greater than about 50° is indicative of a hydrophobic compound. Optical contact angle and methods for calculating it are well known to those skilled in the art using standard evaluation methods and is disclosed in "McGraw-Hill Encyclopedia of Chemistry," 538 (Sybil P. Parker, 2nd ed. 1993) and "Remington's Pharmaceutical Sciences," 256-7 and 294-5 (Arthur Osol et al. eds., 16th ed. 1980), herein incorporated by reference. As such, an effective amount of hydration inhibitor is recognized to be a sufficient amount to shift the optical contact angle of the beneficial agent in association with the hydration inhibitor to at least about 50° and to at least about 70°.

For purposes of illustration and not limitation, the hydration inhibitor includes beneficial agents (including markers), polymeric materials, additives and combinations thereof. When a second "beneficial agent" is used as the hydration inhibitor, the LogP value of the second beneficial agent must be greater than the LogP value of the first beneficial agent. Examples of such beneficial agent hydration inhibitors include antioxidants, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligionucleotides, cell permeation enhancers, radiopaque agents markers and combinations thereof.

Non-limiting examples of specific beneficial agent useful as hydration inhibitors include paclitaxel, rapamycin, rapamycin derivatives, pimecrolimus, everolimus, fenofibrate, carvedilol, taxoteres, tacrolimus, butylated hydroxytoluene, butylated hydroxyanisole, vitamin E, danazol, probucol, tocopherols, tocotrienols, zotarolimus, ABT-627 and analogs, derivatives, or combinations thereof. The following is the chemical structure of ABT-627

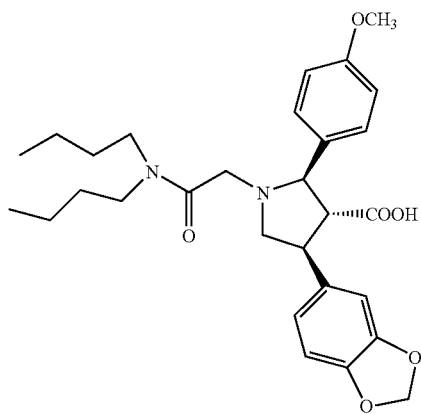

and the chemical structure of zotarolimus is

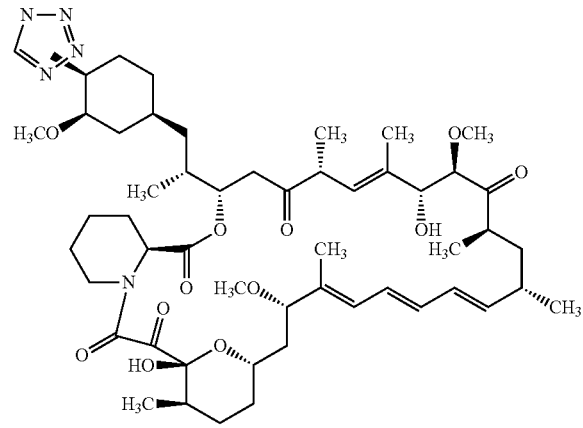

A detailed discussion of ABT-627 (atrasentan) is available in PCT/US02/28776, filed Sep. 10, 2002, and zotarolimus in U.S. Pat. Nos. 6,015,815 and 6,329,386, the disclosure of each is incorporated by reference herein.

Although the hydration inhibitor is associated with the beneficial agent as a mixture, in an alternative embodiment, wherein the hydration inhibitor is a second beneficial agent, the hydration inhibitor can be associated as an overcoat or encapsulating layer covering at least a portion of the first beneficial agent.

Polymeric materials suitable as hydration inhibitors are typically a product of a polymerization reaction inclusive of homopolymers, copolymers, terpolymers, etc., whether natural or synthetic, including random, alternating, block, graft, branched, cross-linked, blends, compositions of blends and variations thereof. The polymer can be in true solution, saturated, or suspended as particles or supersaturated in the beneficial agent. The polymer is biocompatible, and can be biodegradable.

Examples of such polymeric materials include phosphorylcholine, polycaprolactone, poly-D,L-lactic acid, poly-L-lactic acid, poly(lactide-co-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, Parylene®, Parylast®, polyurethane, polycarbonate urethanes, polyethylene, polyethylene terapthalate, ethylene vinyl acetate, ethylene vinyl alcohol, silicone polysiloxanes, substituted polysiloxanes, polyethylene oxide, polybutylene terepthalate-co-PEG, PCL-co-PEG, PLA-co-PEG, polyacrylates, polyvinyl pyrrolidone, polyacrylamide, thermoplastic elastomers, polyolefin elastomers, EPDM rubbers, polyamide elastomers, biostable plastic, acrylic polymers, nylon, polyesters, epoxies and derivatives or combination thereof.

In an embodiment, the polymeric material has a zwitterionic pendant group. In some of the embodiments, the polymer is phosphorylcholine disclosed in U.S. Pat. Nos. 5,705,583 and 6,090,901 to Bowers et al. and U.S. Pat. No. 6,083,257 to Taylor et al, the disclosure of each is incorporated in entirety by reference herewith.

As noted above, the beneficial agent can include a beneficial agent and polymer mixture. In accordance with the method of the invention, the first beneficial agent can correspond to a beneficial agent-polymer mixture having a concentration of polymer to effect the delivery rate of the particular beneficial agent in the beneficial agent mixture. For example, a beneficial agent-polymer mixture having a higher concentration of polymer would have a slower delivery rate of the beneficial agent within the lumen. In contrast, a beneficial agent-polymer mixture having a lower concentration of polymer would cause a more rapid delivery rate of the beneficial agent. The delivery rate is also effected by the difference between the LogP value of the hydration inhibitor and the LogP value of the beneficial agent. For example, generally the greater the difference between the LogP values the greater the retardation of the beneficial agent's delivery rate as compared to the beneficial agent without hydration inhibitor.

Examples of additives suitable as hydration inhibitors include plasticizers, small molecules and oils. Additives are drawn from compounds, polymers, and mixtures without restriction. When used with an interventional device having a polymer coating, an additive is often capable of dispersing through the polymer coating and rendering it effectively more difficult to hydrate as empirically defined as an increase in swelling time in contact with aqueous solution vs. control polymer coating.

Specific non-limiting examples of additives include nitrophenyl octyl ether, bisethylhexyl sebacate, diisododecylphthalate, N-methylpyrrolidone, linolenic acid, linoleic acid, stearic acid, oleic acid, and combinations thereof.

The hydration inhibitor can be associated with the beneficial agent in any of a variety of conventional techniques. As embodied herein, and as previously noted, it is to associate the hydration inhibitor with the beneficial agent as a mixture of the compounds. The mixture can be accomplished by a physical combination in a variety of forms, including solution, suspension, solid interspersion, vapor phase deposition or any physical combination.

An additional aspect of the invention includes the use of a base layer of polymer material to facilitate loading of a beneficial agent on the interventional component. This aspect of the invention is of particular importance if the beneficial agent is difficult or unsuitable for loading alone or in combination with a suitable binder or the like.

When a coating is used in the invention, the coating can include any polymeric material in which the therapeutic agent, i.e., the drug, is substantially soluble. The purpose of the coating is to serve as a controlled release vehicle for the therapeutic agent or as a reservoir for a therapeutic agent to be delivered at the site of a lesion. The coating can be polymeric and can further be hydrophilic, hydrophobic, biodegradable, or non-biodegradable. The material for the polymeric coating can be selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyorthoesters, polyanhydrides, polycarbonates, polypropylenes, polylactic acids, polyglycolic acids, polycaprolactones, polyhydroxybutyrate valerates, polyacrylamides, polyethers, and mixtures and copolymers of the foregoing. Coatings prepared from polymeric dispersions including polyurethane dispersions (BAY-HYDROL, etc.) and acrylic acid latex dispersions can also be used with the therapeutic agents of embodiments of the invention.

Biodegradable polymers that can be used in this invention include polymers including poly(L-lactic acid), poly(DL-lactic acid), polycaprolactone, poly(hydroxy butyrate), polyglycolide, poly(diaxanone), poly(hydroxy valerate), polyorthoester; copolymers including poly (lactide-co-glycolide), polyhydroxy (butyrate-co-valerate), polyglycolide-co-trimethylene carbonate; polyanhydrides; polyphosphoester; polyphosphoester-urethane; polyamino acids; polycyanoacrylates; biomolecules including fibrin, fibrinogen, cellulose, starch, collagen and hyaluronic acid; and mixtures of the foregoing. Biostable materials that are suitable for use in this invention include polymers include polyurethane, silicones, polyesters, polyolefins, polyamides, polycaprolactam, polyimide, polyvinyl chloride, polyvinyl methyl ether, polyvinyl alcohol, acrylic polymers and copolymers, polyacrylonitrile, polystyrene copolymers of vinyl monomers with olefins (including styrene acrylonitrile copolymers, ethylene methyl methacrylate copolymers, ethylene vinyl acetate), polyethers, rayons, cellulosics (including cellulose acetate, cellulose nitrate, cellulose propionate, etc.), parylene and derivatives thereof; and mixtures and copolymers of the foregoing.

A medical devices to which coatings are applied according to the invention can be pretreated to prepare the surfaces for application of coatings. For example, stainless steel stents may be electropolished prior to coating (e.g., undercoat) application. Useful medical devices can be formed from NITINOL alloy, TRIPLEX (stainless steel/tantalum/stainless steel layer) or cobalt chromium alloy. The coatings optionally include a polymeric material, e.g., phosphorylcholine, polycaprolactone, poly-D,L-lactic acid, poly-L-lactic acid, poly (lactide-co-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, Parylene® brand poly-para-xylylene (available from SCSCookson Industries, Indianapolis, Ind.), Paryl AST™ brand biocompatible dielectric polymer (U.S. Pat. Nos. 5,355,832 and 5,447,799, commercially available from AST Products of Billerica, Mass.); polyurethane, polycarbonate urethanes, polyethylene, polyethylene terephthalate, ethylene vinyl acetate, ethylene vinyl alcohol, silicone polysiloxanes, substituted polysiloxanes, polyethylene oxide, polybutylene terephthalate-co-PEG, PCL-co-PEG (i.e., polycaprolactone co-polyethylene glycol), PLA-co-PEG (i.e., polylactic acid-co-polyethylene glycol), polyacrylates, polyvinyl pyrrolidone, polyacrylamide, thermoplastic elastomers, polyolefin elastomers, EPDM rubbers, polyamide elastomers, biostable plastic, acrylic polymers, nylon, polyesters, epoxies and derivatives or blends thereof (e.g., PLLA-phosphorylcholine).

In any of the embodiments disclosed herein, a porous or biodegradable membrane or layer made of biocompatible materials may be coated over the beneficial agent for sustained release thereof, if desired. Alternatively, a suitable base coating capable of retaining beneficial agent therein can be applied uniformly over the surface of the prosthesis, and then selected portions of the base coating can be loaded with the beneficial agent in accordance with embodiments of the invention. A greater amount of beneficial agent can be loaded over a unit surface area intended to have a greater local areal density and a lower amount of beneficial agent can be loaded over a unit surface area intended to have a lower local areal density.

In yet another embodiment of the invention, the beneficial agent may be applied directly to the surface of the prosthesis. Generally a binder or similar component may be used to ensure sufficient adhesion. For example, this coating technique may include admixing the beneficial agent with a suitable binder or polymer to form a coating mixture, which is then coated onto the surface of the prosthesis. The coating mixture would be prepared in higher or lower concentrations of beneficial agent as desired, and then applied to selected portions of the prosthesis appropriately.

As noted above, the beneficial agent may be applied to the interventional component in a polymer, include drug/polymer mixture. The amount of polymer in the mixture is small compared to the amount of drug. For example, the polymer can be about 10% of the amount of drug. In these embodiments, the polymer facilitates processing or loading or enhances retention of the drug on the interventional device, but is in an amount that is not effective to substantially inhibit the hydration of the drug. The presence of the hydration inhibitor of suitable LogP as set forth above has the greater influence on delivery of the drug in this circumstance.

In accordance with some embodiments of the invention, the first and second beneficial agents may correspond to drug-polymer mixtures having different concentrations of polymer to effect different release rates of the particular drug in each beneficial agent. For example, the drug-polymer mixture having a higher concentration of polymer would have a slower release of the drug within the lumen. In contrast, the drug-polymer mixture having a lower concentration of polymer would cause a more rapid release of the drug. Alternatively, rather than providing drug-polymer mixtures having different polymer concentrations to provide different release rates, it is also possible to dispense beneficial agents within different polymers or other binders, wherein the specific polymer or binder has different diffusivity or affinity to assure delivery of the beneficial agents at different rates. Thus, in accordance with the invention, multiple beneficial agents can be released at rates appropriate for their activities and the prosthesis of the invention has multiple beneficial agents that elute off the prosthesis at desired rates.

For example, a cationic phosphorylcholine which has a higher affinity for anionic therapeutic agents can be blended and dispersed as a first beneficial agent and lipophilic phosphorylcholine can be blended with lipophilic drugs as the second beneficial agent to effect different release rates respectively.

As discussed in greater detail below, the beneficial agent(s) and hydration inhibitors can be applied to the medical device in one or more coating layers. For example, alternating layers may be used to control delivery of multiple beneficial agents. Beneficial agents can be applied to the medical device alone or in combination with a suitable hydration inhibitor. Coatings that are suitable for use in this invention include, but are not limited to, any biocompatible polymeric material having suitable mechanical properties and in which the beneficial agent(s) is substantially soluble.

Conventional coating techniques also may be utilized to coat the beneficial agent onto the surface of the prosthesis such as spraying, dipping or sputtering and still provide the desired effect if performed appropriately. With such techniques, it may be desirable or necessary to use known masking or extraction techniques to control the location and amount in which beneficial agent is loaded.

According to some embodiments of the invention, the beneficial agent may be loaded directly onto a component (e.g., by pipetting) or alternatively, the beneficial agent is loaded onto a base material layer that is applied a surface of the component (e.g., dip loading). For example and not limitation, a base coating, such as a binder or suitable polymer, is applied to a selected surface of the interventional component. When desired, a pattern may be formed on a component surface. Beneficial agent is then applied directly to the pattern of the base material. Thus, in accordance with the invention, beneficial agent can be delivered at rates appropriate for the intended use or application.

Figure 5:
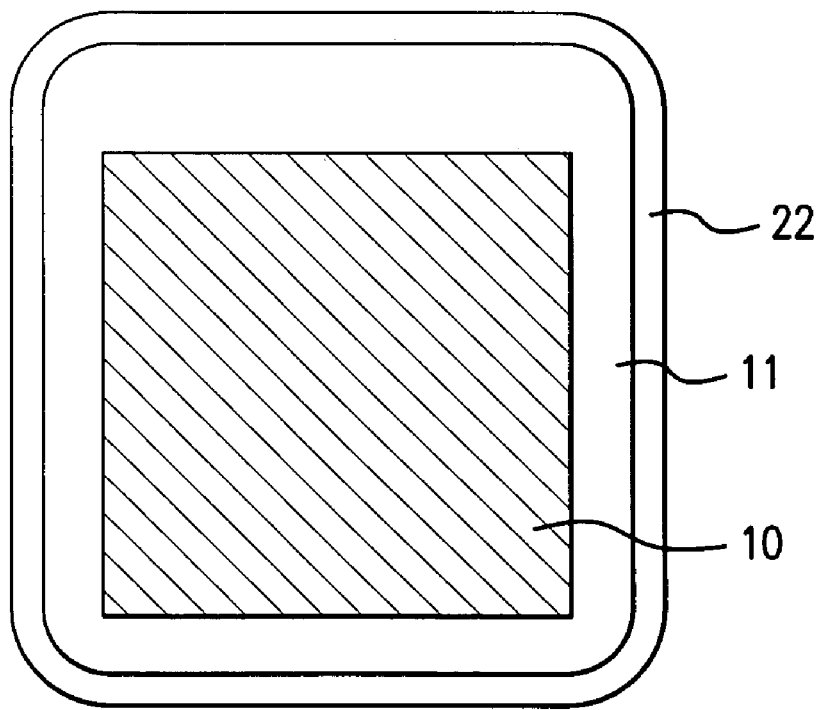
FIG. 5 is a cross-sectional view of a stent strut having a first layer of a beneficial agent and a second layer of a second beneficial agent acting as a hydration inhibitor, according to embodiments of the invention.
Figure 6:
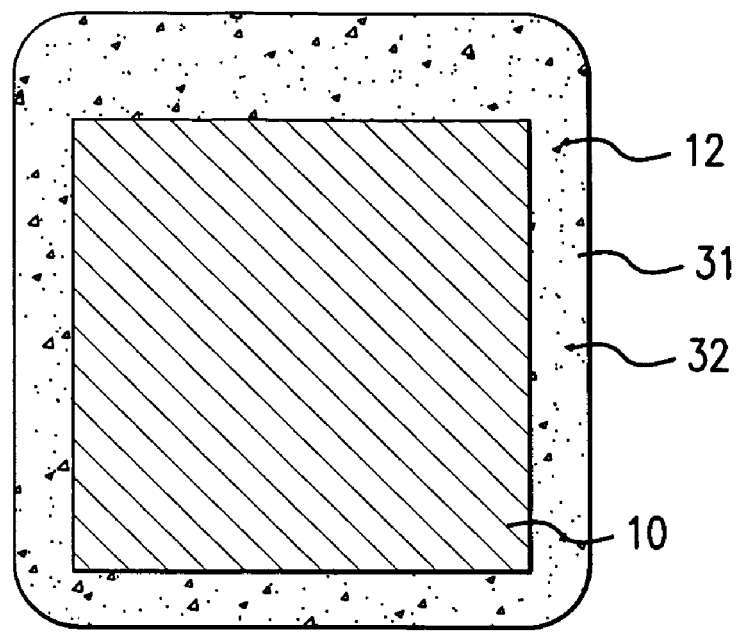
FIG. 6 is a cross-sectional view of a stent strut having a base layer of polymer material which is loaded with a mixture of a beneficial agent and a hydration inhibitor, according to embodiments of the invention.
Figure 7:
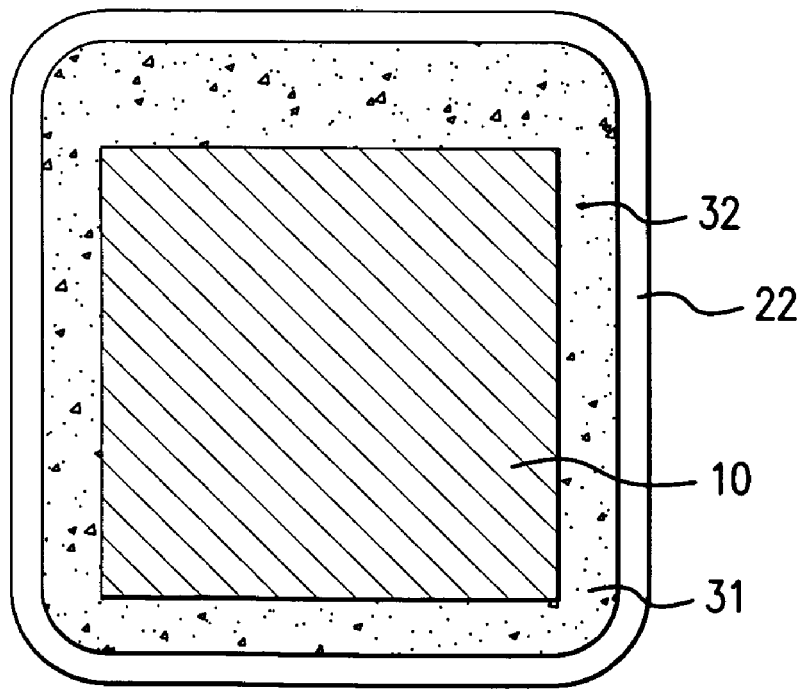
FIG. 7 is a cross-sectional view of a stent strut having a base layer of a polymer material which is loaded with a beneficial agent and a second layer of a second beneficial agent acting as a hydration inhibitor, according to embodiments of the invention.

For purposes of explanation and illustration, and not limitation, exemplary embodiments of the interventional device in accordance with the invention are shown in FIGS. 1-7. In accordance with one aspect of the invention, as shown in FIG. 1, the interventional device is stent 5, having stent struts 10. In an embodiment the interventional device in the form of a stent 5 has a base phosphorylchoine coating in which the beneficial drug is loaded. FIG. 3A shows a cross-sectional view of a vessel segment in which was placed a stent 5 coated with a PC polymer only, and FIG. 3B shows a cross-sectional view of a vessel segment in which was placed a stent 5 coated with a polymer plus drug. To further illustrate the different embodiments of the invention, a cross-sectional view of a stent strut 10 of the stent 5 of FIG. 1 is shown in FIGS. 4-7. In one embodiment of the invention, seen in FIG. 4, the stent strut 10 is loaded with a layer of beneficial agent 11 associated with a hydration inhibitor 12 as a mixture. As embodied herein, the mixture is loaded on the stent strut 10 thicker on one side for increased dosage when desired. In other embodiments not shown, however, the beneficial agent 11 and hydration inhibitor 12 can be loaded evenly throughout or selectively at desired locations on the surface of the interventional component. In a different embodiment of the invention as shown in FIG. 5, the stent strut 10 is loaded with a layer of beneficial agent 11, which is covered by a layer of a second beneficial agent acting as a hydration inhibitor 22. In yet another embodiment of the invention, shown in FIG. 6, the stent strut 10 has a base layer of a polymer material 31, preferably phosphorlycholine, wherein the polymer material is loaded with a beneficial agent 32 associated with a hydration inhibitor 12 as a mixture. FIG. 7 depicts yet another embodiment of the invention wherein a stent strut 10 has a base layer of polymer material 31 loaded with a beneficial agent 32, and a coating of a second beneficial agent acts as a hydration inhibitor 22 to control delivery of the first beneficial agent.

Figure 8:
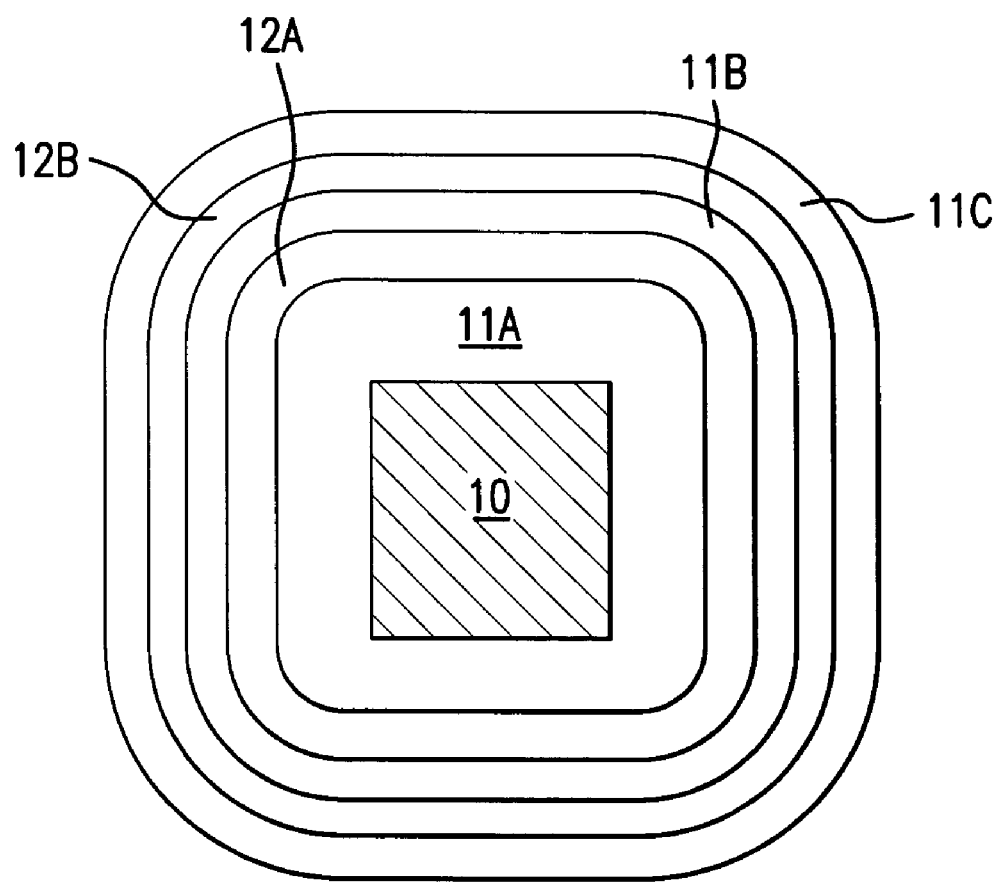
FIG. 8 is a cross sectional view of a stent strut having layers of a first beneficial agent alternating with layers of a second beneficial agent/hydration inhibitor, according to embodiments of the invention.

Furthermore, in a different embodiment of the invention as seen in the cross sectional view of FIG. 8 a stent strut 10 has layers 11A, 11B and 11C of a first beneficial agent alternating with layers 12A and 12B of a second beneficial agent/hydration inhibitor. According to this embodiment, first beneficial agent, e.g., estradiol, from layer 11C elutes in an initial burst. Second beneficial agent/hydration inhibitor, e.g., zotarolimus, in layer 12B controls elution of first beneficial agent from layer 11B. Thus, the LogP value of the second beneficial agent/hydration inhibitor is greater than the LogP value of the first beneficial agent, in accordance with principles of the invention. Similarly, second beneficial agent/hydration inhibitor in layer 12A controls elution of first beneficial agent in layer 11A. Layers 12A and 12B enable midterm and late term delivery of first beneficial agent along with second beneficial agent/hydration inhibitor. Depending on the beneficial agents selected, layers 11A, 11B, 11C, 12A and 12B may optionally contain a polymer carrier or binder or other additive to facilitate processing or retention of the beneficial agent on the interventional device.

As those skilled in the art will appreciate, many variations of this embodiment are possible, depending on the medical condition(s) being treated, number and identity of beneficial agents selected, desired order of delivery and other factors. For example, layers 11A, 11B and 11C need not include the same beneficial agent. Each can include a different beneficial agent or two can include the same beneficial agent with the third including another beneficial agent. Similarly, layers 12A and 12B need not contain the same beneficial agent. Although not shown here, even more complicated variations can be achieved by those skilled in the art using the principles disclosed herein. For example, it may be desirable to achieve a relatively early delivery of estradiol to treat surface monocytes and a delayed delivery of dexamethasone to treat tissue monocytes and macrophages.

In an embodiment of the invention, the hydration inhibitor has a LogP value of greater than 4.5 units and the beneficial agent has a LogP value less than 3 units. In this manner, the hydration inhibitor acts as a water barrier for the less hydrophobic beneficial agent, thereby reducing the release rate of the beneficial agent. For example and not limitation, the less hydrophobic beneficial agent can be ABT 620 {1-Methyl-N-(3,4,5-trimethoxyphenyl)-1H-indole-5-sulfonamide}, ABT 627, ABT 518 {[S-(R*,R*)]-N-[1-(2,2-dimethyl-1,3-dioxol-4-yl)-2-[[4-[4-(trifluoro-methoxy)-phenoxy]phenyl]sulfonyl]ethyl]-N-hydroxyformamide}, dexamethasone and the like and the hydration inhibitor can be Fenofibrate, Tricor™ or 3S,6R,7E,9R,10R,12R,14S,15E,17E,19E,21S,23S,26R, 27R,34aS)-9,10,12,13,14,21,22,23,24,25,26,27,32,33,34, 34a-Hexadecahydro-9,27-dihydroxy-3-[(1R)-2-[(1S,3R, 4R)-3-methoxy-4-tetrazol-1-yl)cyclohexyl]-1-methylethyl]-10,21-dimethoxy-6,8,12,14,20,26-hexamethyl-23,27-epoxy-3H-pyrido[2,1-c][1,4]oxaazacyclohentriacontine-1, 5,11,28,29(4H,6H,31H)-pentone; 23,27-Epoxy-3H-pyrido [2,1-c][1,4]oxaazacyclohentriacontine-1,5,11,28,29(4H,6H, 31H)-pentone.

The intervention component can include at least one reservoir or cavity therein. In accordance with another aspect of the invention, one or more of the reservoirs or cavities is loaded with a more hydrophilic first beneficial agent and then a second more hydrophobic beneficial agent can be loaded onto the first beneficial agent within the cavity or reservoir in a manner as described above.

In another embodiment of the invention, the interventional device can include a third beneficial agent. The third beneficial agent can be any of the beneficial agents disclosed above. In an embodiment the third beneficial agent covers the second beneficial agent, the third beneficial agent having a LogP value less than the second LogP for rapid release of the third beneficial agent. In this embodiment the third beneficial agent can be the same as the first, so the beneficial agent is released rapidly upon implantation followed by a controlled release of the beneficial agent.

The invention also provides a method for manufacturing a medical device for controlled delivery of beneficial agent. This method comprises the steps of providing an interventional component to be deployed in a patient; loading a beneficial agent on the interventional component for delivery therefrom, the beneficial agent having a first LogP value; and associating an effective amount of a hydration inhibitor with the beneficial agent to control delivery of the beneficial agent from the interventional component, the hydration inhibitor having a second LogP value, the second LogP value being greater than the first LogP value.

A number of methods can be used to load the beneficial agent onto the surface of the interventional component to provide for a controlled local areal density of beneficial agent. For example, the interventional component can be constructed to include pores or reservoirs which are impregnated or filled with beneficial agent, alone or in combination with a hydration inhibitor. The pores can be sized or spaced apart to correspond to or limit the amount of beneficial agent contained therein in accordance with the desired local areal density pattern along the length of the interventional device, wherein larger pores or more dense spacing would be provided in such portions intended to have a greater local areal density.

According to various embodiments of the invention, the beneficial agent can be loaded directly onto the interventional component or alternatively, the beneficial agent is loaded onto a base material layer that is applied to at least a portion of the interventional component. For example and not limitation, a base coating, including a binder or suitable polymer, is applied to a selected surface of the interventional component such that a desired pattern is formed on the interventional component surface. Beneficial agent and hydration inhibitor is then applied directly to the pattern of the base material. Generally, "controlled areal density" is understood to mean a known or predetermined amount of beneficial agent or mixture of beneficial agent and hydration inhibitor, either by weight or volume, over a unit surface area of the interventional component. In one aspect of the invention, the desired pattern corresponds to the desired controlled local areal density. For example, a greater amount of base material layer is applied to portions of the interventional device intended to have a greater local areal density of beneficial agent, and a lesser amount of base material is applied to portions of the interventional device intended to have a lower local areal density of beneficial agent. In yet another embodiment of the invention, the beneficial agent can be applied directly to the surface of the interventional component.

Conventional coating techniques also can be utilized to coat the beneficial agent onto the surface of the interventional component such as spraying, dipping or sputtering and still provide the desired effect if performed appropriately. With such techniques, it can be desirable or necessary to use known masking or extraction techniques to control the location and amount in which beneficial agent is loaded. See U.S. patent application Ser. No. 09/950,307, filed Sep. 10, 2001; U.S. Pat. Nos. 6,329,386 and 6,015,815; and U.S. Patent Provisional Application entitled, "Medical Device Having a Hydration Inhibitor," filed on Mar. 10, 2003, each of which is incorporated herein by reference.

In yet another aspect of the invention, the beneficial agent(s) described herein can be applied to an intervention component that has been coated with a polymeric compound. Incorporation of the compound or drug into the polymeric coating of the interventional component can be carried out by dipping the polymer-coated interventional component into a solution containing the compound or drug for a sufficient period of time (such as, for example, five minutes) and then drying the coated interventional component, preferably by means of air drying for a sufficient period of time (such as, for example, 30 minutes). The polymer-coated interventional component containing the compound or drug can then be delivered to the coronary vessel by deployment from a balloon catheter, for example.

In another embodiment, the beneficial agent and hydration inhibitor is "printed" onto the surface of the interventional component by a fluid-dispenser having a dispensing element capable of dispensing beneficial agent in discrete droplets, wherein each droplet has a controlled trajectory. In particular, the beneficial agent or mixture is selectively dispensed from the dispensing element to a predetermined portion of the interventional component in a raster format along a dispensing path. Advantageously, fluid-jetting technology can be used to deposit materials, such as beneficial agents and hydration inhibitors, in controlled volumes onto a substrate at a controlled location. See U.S. Provisional Patent Application Nos. 60/424,575; 60/424,577; 60/424,607; 60/424,574; and 60/424,576, all filed Nov. 7, 2002, each is incorporated by reference herein.

Further in accordance with the invention, the first beneficial agent loaded onto the interventional component has a first local areal density and the second beneficial agent loaded onto the interventional component has a second local areal density. As used herein, "areal density" refers to the amount of beneficial agent per unit surface area of a selected portion of the interventional component. "Local areal density" refers to the dosage of beneficial agent per local surface area of the interventional component. The local areal density of the first beneficial agent and the local areal density of the second beneficial agent can be uniform across each respective portion to define stepped changes in local area density or can be varied across a selected portion of the interventional component to define gradients of local area density. Accordingly, a medical device is provided having an interventional component that is at least partially loaded with beneficial agent having a local areal density that is varied along a selected portion of the body of the interventional component.

In accordance with the invention, the local areal density can be varied by varying the relative rate in which beneficial agent is loaded to a selected location along the interventional component. To this end, the frequency in which the droplets of beneficial agent are applied along a unit length of the dispensing path to the interventional component is varied. Alternatively, the relative rate of loading beneficial agent can be varied by varying the relative movement between the dispensing element and the interventional component. Another alternative for varying the relative rate of loading beneficial agent is to vary the amount of beneficial agent per droplet dispensed from the dispensing element. Other alternatives for varying the local areal density of beneficial agent loaded onto the interventional component include mixing the beneficial agent with a binder and varying the ratio of beneficial agent to binder. Alternatively, the amount of the mixture of beneficial agent and binder that is applied to the interventional component can be varied to achieve a varied local areal density of beneficial agent. However, other methods of varying the local areal density of beneficial agent known in the art can be used.

In accordance with another embodiment of the invention, the first surface of the interventional component is defined by a plurality of interconnecting structural members. Accordingly, the first surface can include a first selected set of structural members, e.g., a connector member, and the second surface can include a second selected set of the structural members, e.g., a ring-shaped element extending around the circumference of the interventional component.

Another feature of the invention includes applying a layer of base material on a selected portion of the interventional component described above. The beneficial agent or mixture with hydration inhibitor is loaded onto the base material layer according to the methods described above. The base material layer can define a pattern for loading the beneficial agent onto the interventional component.

The invention will be further understood by the examples set forth below, which are provided for purpose of illustration and not limitation.

EXAMPLES

Example 1

Elution Experiments of Beneficial Agents

I. Coating the Coupon with PC1036

Figure 9A:
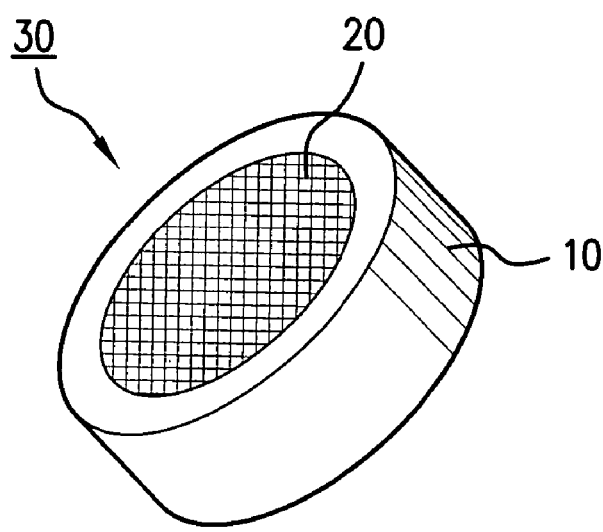
FIG. 9A is a top view of a drug-loaded coupon, according to embodiments of the invention.
Figure 9B:
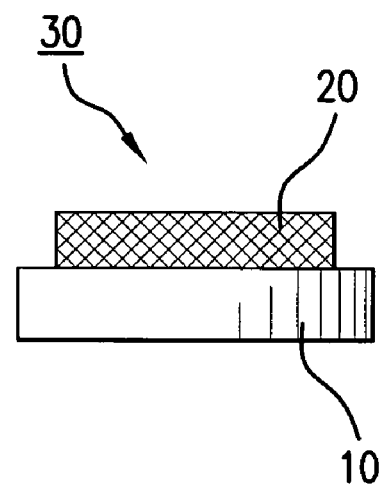
FIG. 9B is a side view of a drug-loaded coupon according to embodiments of the invention.

Prior to any experimentation, coated stainless steel coupons were prepared. These coupons were 316L electropolished stainless steel discs (10 mm diameter). This size was chosen because the surface area of one side of the coupon is similar to the surface area of a 15-mm open cell BiodivYsio stent. The coupon was prepared by scratching a mark on one side of the coupon, to indicate the side of the coupon that will not be coated, and then cleaned. The cleaning was a two-step process in which the coupons are sonicated for 3 minutes in dichloromethylene and 3 minutes in ethanol. The coupons were allowed to dry at room temperature. One side of the coupon was coated using a filtered 20-mg/mL solution of phosphoryl choline polymer PC1036 (product of Biocompatibles Ltd., Farnham, Surrey, UK) in ethanol. Twenty µL PC solution was placed onto the coupon using a gas tight glass syringe, ensuring that the entire surface was coated but not spilling over the sides of the coupon. The coupons were initially air dried and then cured at 70° C. for 16 hours. They were then sent for gamma irradiation at <25 KGy. The resulting PC coating thickness was close to that of the stent and thick enough to accommodate the desired loaded drug dose, as graphically represented in FIG. 9A-B. FIG. 9A-B is a top and side view of a coated stainless steel coupon 30, having a PC-coating 20 on a electropolished stainless steel disc.

II. Loading the Coupon with Drugs of Interest

In these experiments, beneficial agents were loaded onto coupons and elution profiles examined. In general, the procedure is as follows. Twelve PC-coated coupons were loaded with each drug. The solutions of the drugs were usually 5.0 mg/mL in 100% ethanol and were filtered with a 0.45 µm filter prior to use.

The coupons were weighed before loading with the drug solution. To load 100 µg of drug, 20 µL of solution was placed (e.g., pipetted) on the center of the PC coated side of the coupon. The coupon was placed in a vial for 30 minutes with the lid closed to allow the drug to penetrate the coating. The lid was removed and the coupon was allowed to dry for an additional 90 minutes. To ensure that the coupon was completely dry, the coupon was weighed, and after 15 minutes the coupon was weighed a third time. When two weightings of the coupon were the same, the coupon was considered dry. The loaded, dry coupons were stored in a refrigerator protected from light.

III. Extracting Drugs from the Coupon

For each drug, six coupons were used to evaluate the total amount of drug loaded by the above procedure. The coupons were immersed in 5 mL of 50% ethanol, 50% water solution and sonicated for 1 hour. The concentration of the drug in the extraction solution was analyzed by HPLC.

At the end of the elution experiments discussed below, the coupons were removed from the elution media and immersed in 5 mL of 50% ethanol, 50% water solution and sonicated for 1 hour. The concentration of the drug in these vials indicated the amount of the drug remaining in the coupons at the end of the elution experiments.

IV. Elution Process

Six coated coupons of each drug were used for the elution experiments. The coupons were individually placed, coating side up, in small metal cups to hold the coupon and to allow movement to a new vial at each time point. The coupons were usually placed in a vial containing 10 mL of pH 7.4 phosphate buffered saline. The vials were stored in an orbital shaker, with horizontal shaking of 100 rpm, at 37° C. for at least 30 minutes before insertion of a coupon to allow the solution to equilibrate at the desired temperature. At least nine different time points were observed as shown in Table 2. After the desired time had lapsed, the coupon holder was lifted and allowed to drain. It was then placed into a pre-warmed vial corresponding to the next time point. This procedure continued until the predetermined time had elapsed. At that point, the coupons went through a drug extraction step as outlined earlier. The amount of drug in the elution samples was determined by HPLC.

To illustrate the effect of a relatively less hydrophilic beneficial agent/hydration inhibitor on a relatively more hydrophilic beneficial agent (i.e., a combination drugs) several different loading procedures were investigated. In particular for zotarolimus and dexamethasone combination the following were investigated.

TABLE 2

One-Day Elution Study Time and Sample Size

| Sample Number | Elution Time (Days) | Elution Time (Hours) | Elution Volume (mL) |
|---|---|---|---|
| 1 | 0.003 | 0.08 (5 min) | 10 |
| 2 | 0.010 | 0.25 (15 min) | 10 |
| 3 | 0.021 | 0.50 (30 min) | 10 |
| 4 | 0.042 | 1 | 10 |
| 5 | 0.083 | 2 | 10 |
| 6 | 0.125 | 3 | 10 |
| 7 | 0.167 | 4 | 10 |
| 8 | 0.208 | 5 | 10 |
| 9 | 0.250 | 6 | 10 |

FIGS. 10, 11, 12, 13 and 14 illustrate the effect of a hydration inhibitor according to the invention on the elution of a relatively more hydrophilic beneficial agent. In FIGS. 10-13, the drugs were applied to coupons; in FIG. 14, stents were coated.

Figure 10:
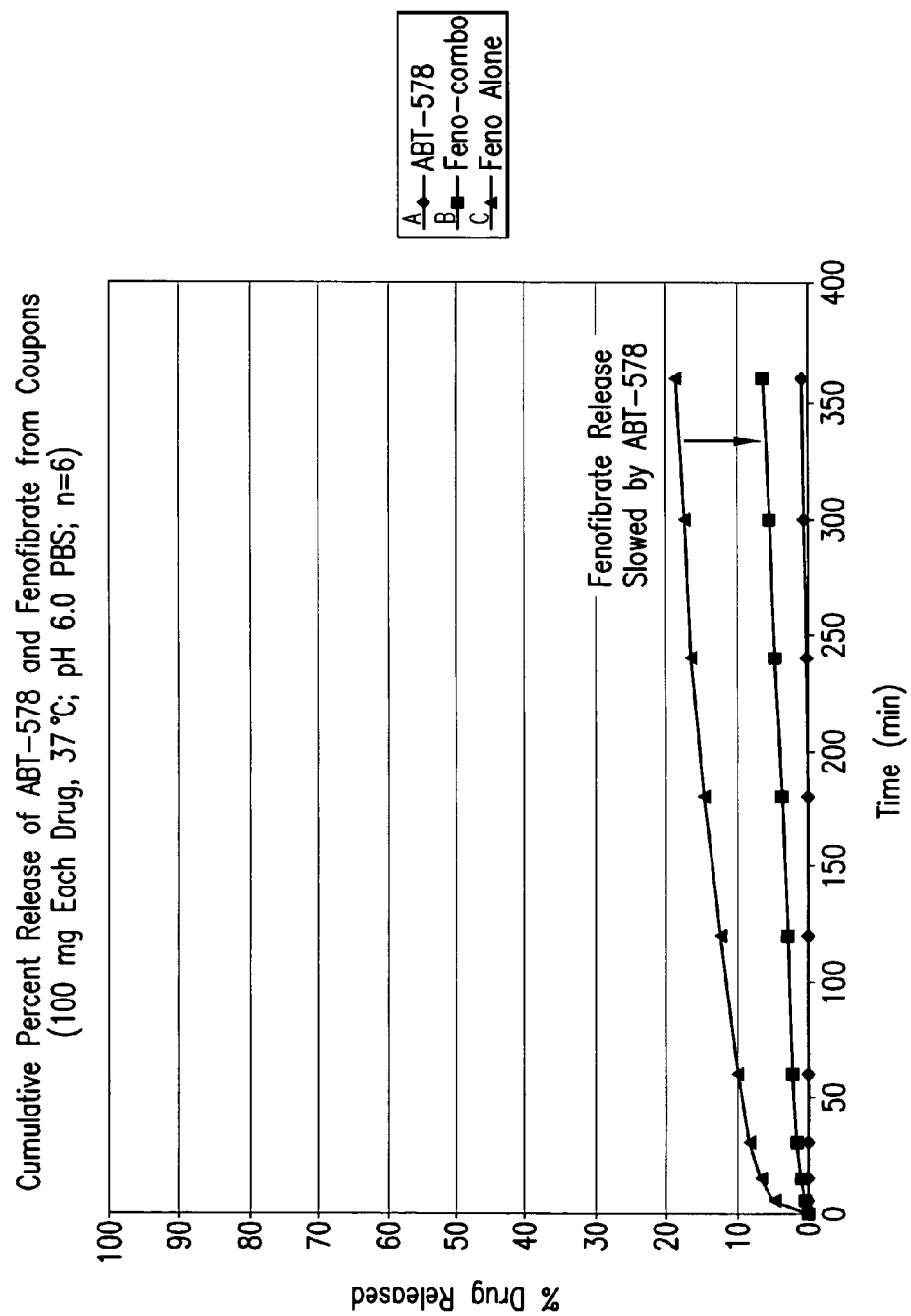
FIG. 10 is a graph showing the six-hour elution profile of the beneficial agent fenofibrate and the hydration inhibitor zotarolimus (ABT-578), according to embodiments of the invention.

In FIG. 10, the six-hour elution profile shown is where the beneficial agent is fenofibrate and the hydration inhibitor is zotarolimus. Elution was carried out as described above. Curve A is the elution profile of zotarolimus alone. Curves B and C are the profiles for fenofibrate, in combination with zotarolimus and alone, respectively. Curve B shows that only about 7% of the fenofibrate was released from the coupon after 6 hours. As can be seen by comparing Curves B and C, the release of fenofibrate was significantly reduced by the presence of zotarolimus.

Figure 11:
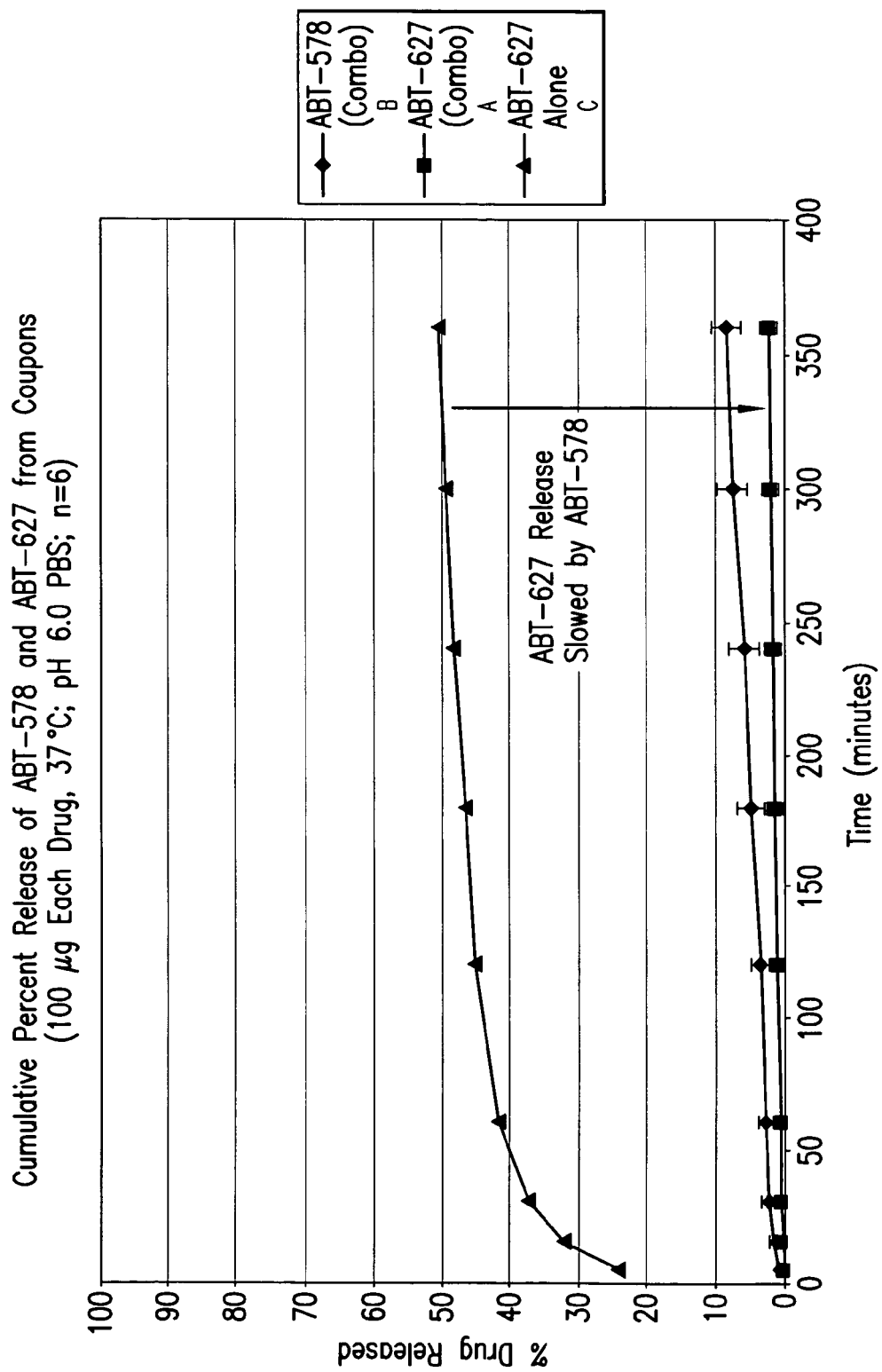
FIG. 11 is a graph showing the six-hour elution profile of beneficial agent ABT-627 (atrasentan) in the presence of hydration inhibitor zotarolimus, according to embodiments of the invention.

FIG. 11 illustrates the six-hour elution profile of beneficial agent ABT-627 (atrasentan) in the presence of hydration inhibitor zotarolimus. Curves A and C are the elution profiles of ABT-627, in the presence of zotarolimus and alone, respectively. Curve B shows the elution of zotarolimus under the same conditions. Comparing Curves A and C, it is seen that the elution rate of relatively more hydrophilic ABT-627 is reduced in the presence of relatively less hydrophilic zotarolimus. After six hours, much less than 10% of ABT-627 was released in the presence of zotarolimus (Curve C), compared to 50% in the absence of zotarolimus (Curve A).

Figure 12:
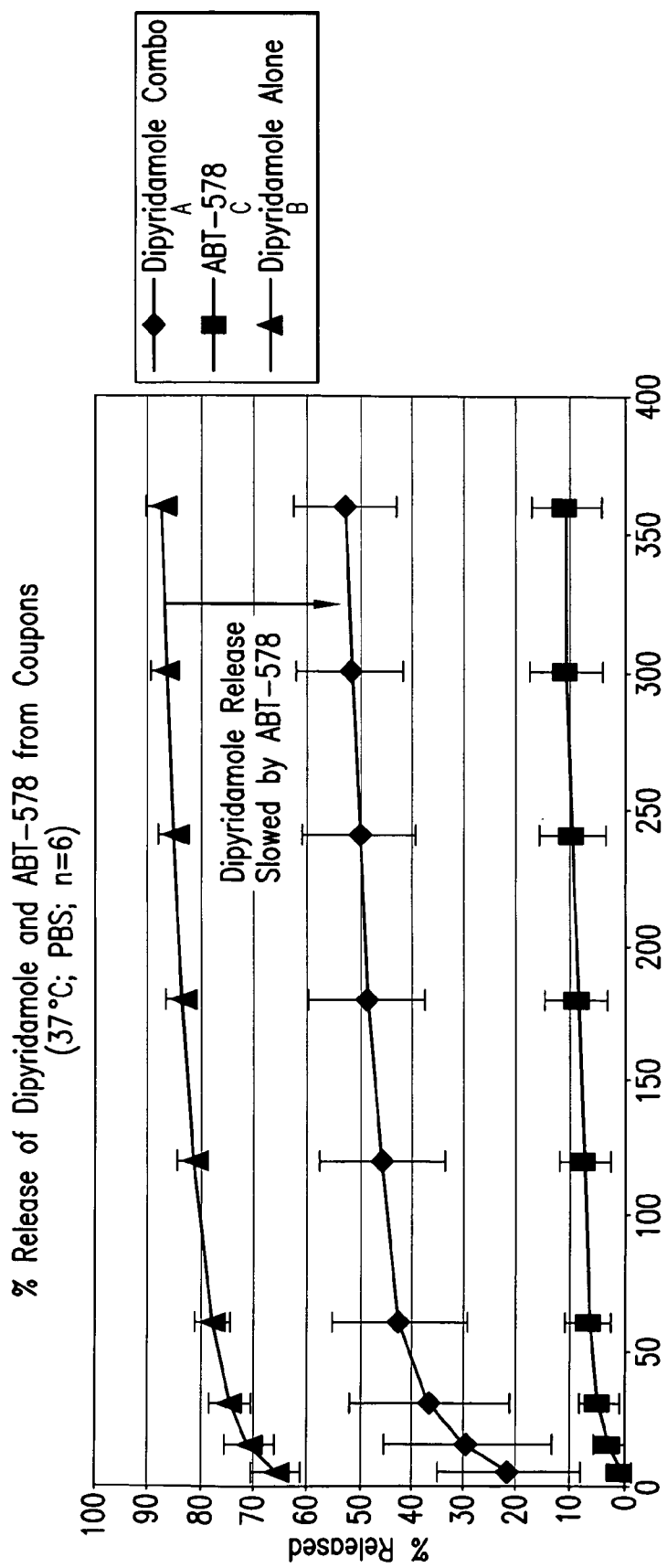
FIG. 12 is a graph showing the six-hour elution profile of beneficial agent dipyridamole in the presence of hydration inhibitor zotarolimus, according to embodiments of the invention.

FIG. 12 illustrates the six-hour elution profile of beneficial agent dipyridamole in the presence of hydration inhibitor zotarolimus. Curves A and B are the elution profiles of dipyridamole, in the presence of zotarolimus and alone, respectively. Curve C shows the elution profile of ABT 578 under the same conditions. As can be seen by comparing Curves A and B, the amount of dipyridamole released from the coupons coated with zotarolimus and dipyridamole is only about 52% after six hours, compared to nearly 90% in the absence of zotarolimus.

Figure 13:
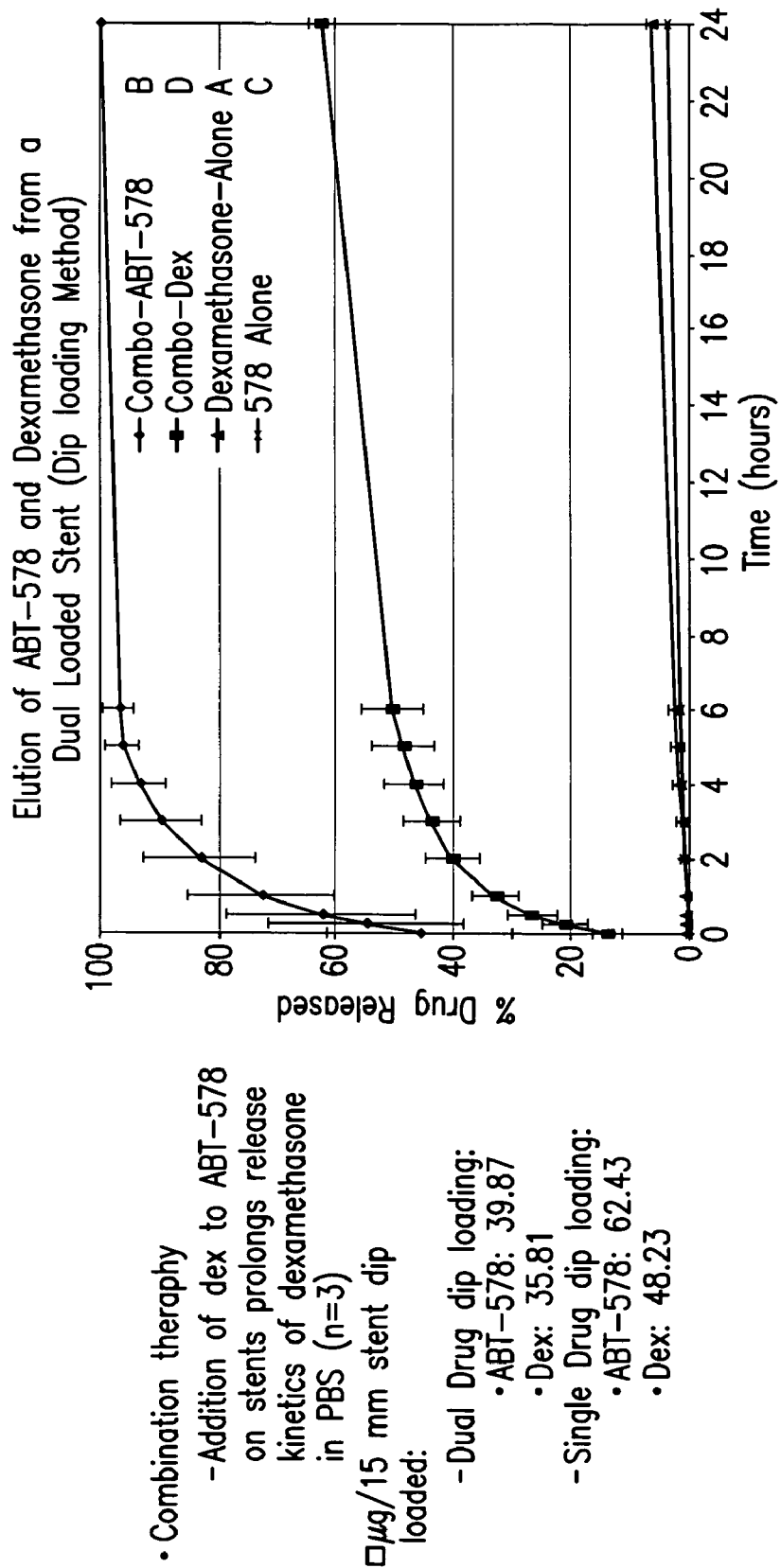
FIG. 13 is a graph showing the six hour elution profiles of beneficial agent dexamethasone in the presence of hydration inhibitor zotarolimus, according to embodiments of the invention.

FIG. 13 illustrates the six-hour elution profiles of beneficial agent dexamethasone in the presence of hydration inhibitor zotarolimus. Curves A and B are the elution profiles of dexamethasone, alone and in the presence of zotarolimus, respectively. Curves C and D (superimposed) are the elution profiles for zotarolimus, alone and in the presence of dexamethasone, respectively, under the same conditions. As can be seen by comparing Curves A and B, the amount of dexamethasone remaining on the coupon containing dexamethasone and zotarolimus was nearly 70% compared to only 25% on the coupon on which no zotarolimus was present.

Figure 14:
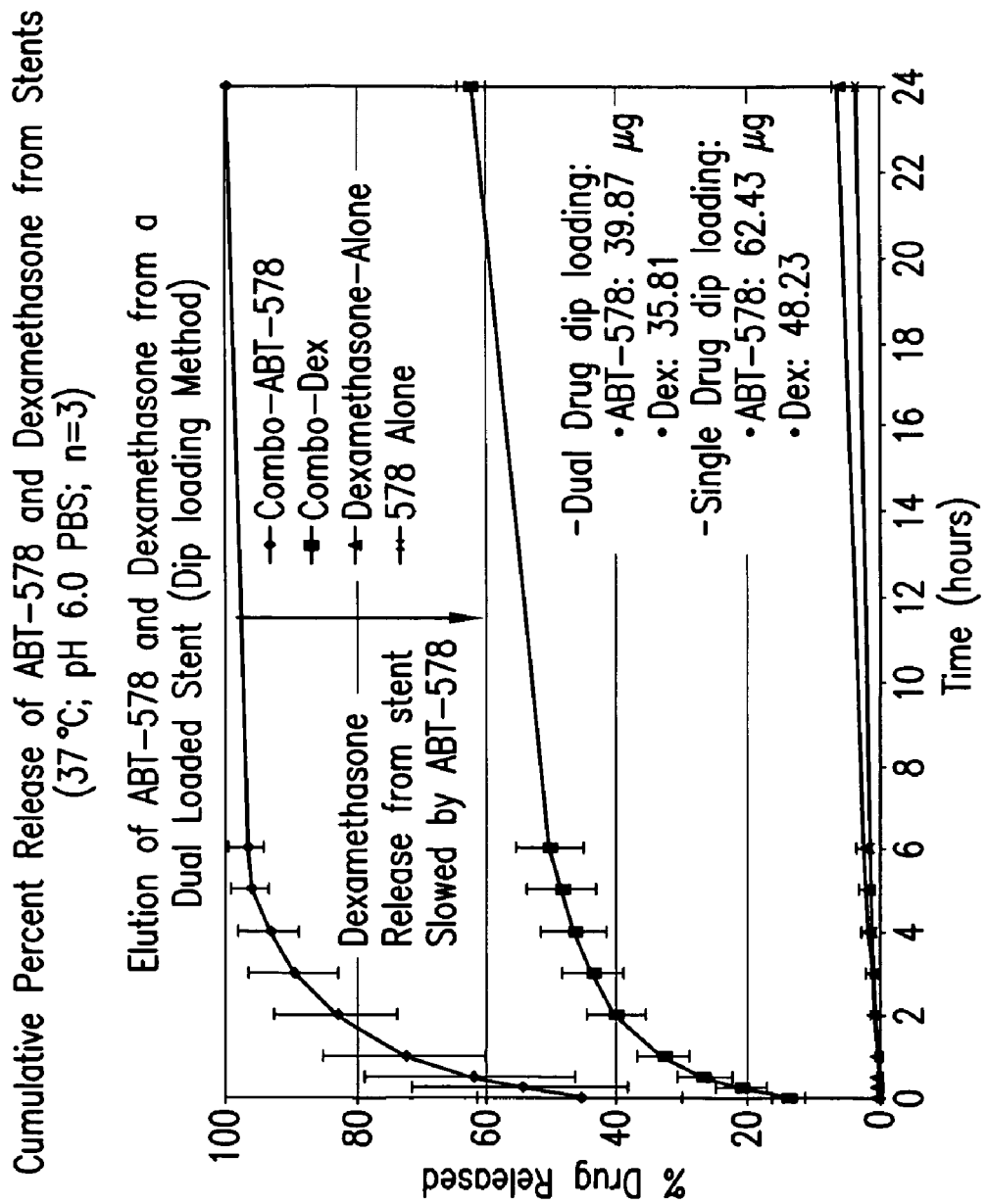
FIG. 14 is a graph showing the six-hour elution profile of beneficial agent dexamethasone in the presence of hydration inhibitor zotarolimus on a PC-coated stent, according to embodiments of the invention.

FIG. 14 illustrates the six-hour elution profile of beneficial agent dexamethasone in the presence of hydration inhibitor zotarolimus on a PC-coated stent. Loading was accomplished by dip loading, that I,s a stent was dipped into a solution containing either one or both drugs and then permitted to dry. Curves A and B are the elution profiles for dexamethasone in the presence of zotarolimus and alone, respectively. Curves C and D are the elution profiles for zotarolimus in the presence of dexamethasone and alone, respectively. As can be seen by comparing Curves A and B, after 24 hours, almost no dexamethasone was released from the stent containing zotarolimus and dexamethasone, though about 40% of the dexamethasone was released from the stent having no zotarolimus present in the coating.

Example 2

Elution Experiments of Dexamethasone from Stents

I. Coating the Stents with PC1036

Prior to any experimentation, coated stents were prepared. These were 3.0 mm×15 mm 316L electropolished stainless steel stents. Each stent was spray coated using a filtered 20-mg/mL solution of phosphoryl choline polymer PC1036 (product of Biocompatibles Ltd., Farnham, Surrey, UK) in ethanol. The stents were initially air dried and then cured at 70° C. for 16 hours. They were then sent for gamma irradiation at <25 KGy.

II. Loading the Stents with Drugs of Interest

In these experiments, beneficial agents were loaded onto stents and elution profiles examined. In general, the procedure was as follows. Multiple PC-coated stents were loaded with each drug combination solution. The solutions of the drugs were usually in the range of 2-20 mg/mL of zotarolimus and 10.0 mg/mL dexamethasone in 100% ethanol, with ~10% PC1036 added to the solution to enhance film formation.

The stents were weighed before loading with the drug solution. To load approximately 10 µg/mL of each drug, a solution with equal amounts of zotarolimus and dexamethasone was sprayed onto the stent in a controlled fashion. The stent was allowed to dry before the stents were re-weighted to determine total drug load. The loaded, dry stents were stored in a refrigerator and were protected from light.

III. Extracting Drugs from the Stent

For each drug, 3 stents were used to evaluate the total amount of drug loaded by the above procedure. The stents were immersed in 6 mL of 50% ethanol, 50% water solution and sonicated for 20 minutes. The concentration of the drug in the extraction solution was analyzed by HPLC.

At the end of the accelerated elution experiments discussed below, the stents were removed from the dissolution media and immersed in 5 mL of 50% ethanol, 50% water solution and sonicated for 20 minutes. The concentration of the drug in these vials indicated the amount of the drug remaining on the stents at the end of the accelerated elution experiments. In this way, drug extraction was measured.

IV. Accelerated Elution Process

An HPLC method was developed for the determination of the amount of zotarolimus and dexamethasone eluted from phosphorylcholine (PC) coated metal stents (described above) in dissolution studies using an aqueous solution of polyethylene glycol 660 buffered at pH 4 as the dissolution medium. The method is used to determine the amount of drug that has eluted from the stent into the dissolution medium at 37° C. at selected time points, typically in a 24-hour period. This rapid, in vitro elution test is intended for use as a quality check on the manufacturing process and a fast reliable research tool for understanding the factors controlling elution of drugs from stents.

Two coated stents of each drug combination ratio were used for the accelerated elution experiments. The stents were individually dropped into the 1 liter containers of the dissolution bath apparatus containing 500 mL of dissolution medium at 37° C. The dissolution bath stirring paddles operated at 50 rpm. An autosampler was programmed to pull samples at multiple time points (Table 4). This procedure continued until the predetermined time had elapsed. At that point, the stent went through a drug extraction step as outlined earlier. The amount of drug in the elution samples was determined by HPLC.

To illustrate the effect of a relatively less hydrophilic beneficial agent/hydration inhibitor on a relatively more hydrophilic beneficial agent (i.e., a combination drugs) several different loading ratios were investigated. In particular, for zotarolimus/dexamethasone (zotarolimus/dex) combinations, the following were investigated at the ratios and loading solution concentrations set forth in Table 3, below.

TABLE 3

Loading Solution Ratios

| Solution Ratio Zotarolimus:Dex | Concentration Dexamethasone | Concentration Zotarolimus | Concentration PC1036 | Number of Stents |
|---|---|---|---|---|
| 1:2 | 10 mg/ml | 20 mg/ml | 3 mg/ml | 6 |
| 1:1 | 10 mg/ml | 10 mg/ml | 2 mg/ml | 6 |
| 4:3 | 10 mg/ml | 7.5 mg/ml | 1.75 mg/ml | 6 |
| 2:1 | 10 mg/ml | 5 mg/ml | 1.5 mg/ml | 6 |
| 5:1 | 10 mg/ml | 2 mg/ml | 1.2 mg/ml | 6 |

TABLE 4

One-Day Accelerated Elution Study Time Points

| Data Point | Time Points (minutes) |
|---|---|
| 1 | 5 |
| 2 | 10 |
| 3 | 15 |
| 4 | 30 |
| 5 | 45 |
| 6 | 60 |
| 7 | 90 |
| 8 | 120 |
| 9 | 150 |
| 10 | 180 |
| 11 | 240 |
| 12 | 300 |
| 13 | 360 |
| 14 | 420 |
| 15 | 480 |
| 16 | 720 |
| 17 | 960 |
| 18 | 1200 |
| 19 | 1440 |

Figure 15:
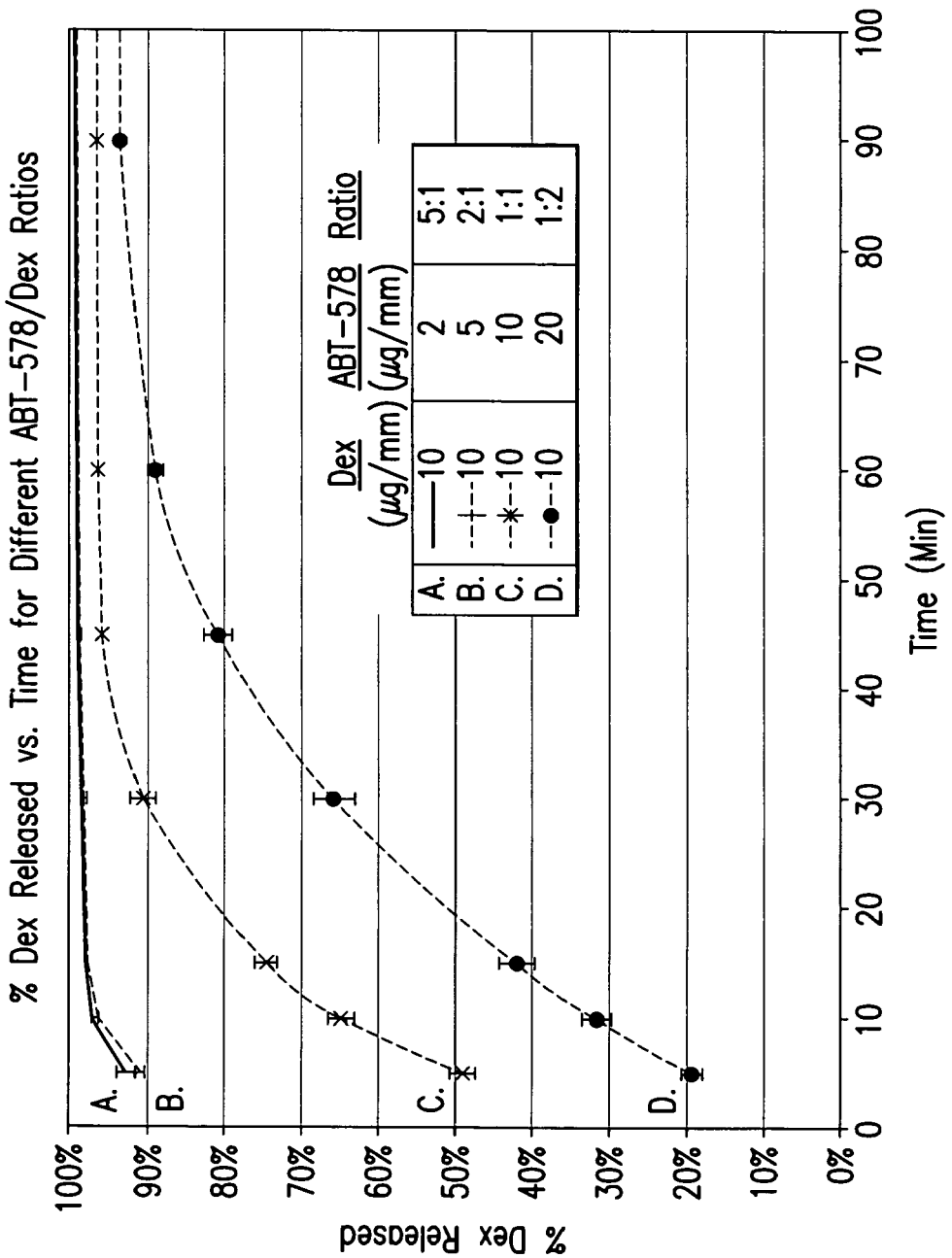
FIG. 15 is a graph showing the accelerated elution profiles of beneficial agent dexamethasone in the presence of hydration inhibitor zotarolimus at different zotarolimus-to-dexamethasone ratios, according to embodiments of the invention.

FIG. 15 illustrates the effect of a hydration inhibitor according to the invention on the elution of a relatively more hydrophilic beneficial agent from, for example, a stent.

In particular, FIG. 15 illustrates accelerated elution profiles (generated for example, by the technique described above) of beneficial agent dexamethasone in the presence of hydration inhibitor zotarolimus at different ratios. Curves A and B are the accelerated elution profiles of dexamethasone. As can be seen from the table in the plot, the amount of dexamethasone is higher than zotarolimus. Curves C and D show the accelerated elution profiles for dexamethasone. In these curves, the ratio of zotarolimus-to-dexamethasone increases to 1:1 and 2:1. As can be seen by comparing Curves A through D, dexamethasone elution becomes increasingly slow with increasing zotarolimus concentration. Thus, the amount of dexamethasone remaining on a zotarolimus/dexamethasone coated stent increases as the ratio of zotarolimus-to-dexamethasone increases.

Thus zotarolimus acts as an elution inhibitor for the more hydrophilic dexamethasone, further supporting the conclusion that relatively less hydrophilic beneficial agents can act as hydration inhibitors of relatively more hydrophilic agents.

Example 3

Protection of Dexamethasone from Degradation by the Presence of Zotarolimus

I Dexamethasone/Zotarolimus/PC Coated Stents

In these experiments, beneficial agents were loaded onto stents and the stability of the two drugs was examined. In general, the procedure was as follows. Multiple PC-coated stents were loaded with each drug combination from solution. The solutions of the drugs were usually in the range of 2-20 mg/mL of zotarolimus and 10.0 mg/mL dexamethasone in 100% ethanol, with ~10% PC1036 added to the solution to enhance film formation.

The stents were weighed before loading with the drug solution. To load approximately 10 μg/mL of each drug, a solution with equal amounts of zotarolimus and dexamethasone was sprayed onto the stent in a controlled fashion. The stent was allowed to dry before the stents were re-weighed to determine total drug load. The loaded, dry stents were stored in a refrigerator and were protected from light.

II. ETO Sterilization of Stents

After drug loading, stents were crimped onto catheter balloons and packaged into medical product Tyvek pouches for ETO (ethylene oxide) sterilization. The ETO sterilization process is standard in the medical device industry to ensure product safety. The ETO process was performed in a high humidity, elevated temperature environment to ensure microbe and spore kill.

III. Extracting Drugs from the Stent

For each drug, multiple stents were used to evaluate the purity and stability of the drug loaded by the above procedure. The stents were immersed in 6 mL of 50% ethanol, 50% water solution and sonicated for 20 minutes. The concentration and the presence of degradant-related impurities of the drug in the extraction solution were analyzed by HPLC.

Figure 16:
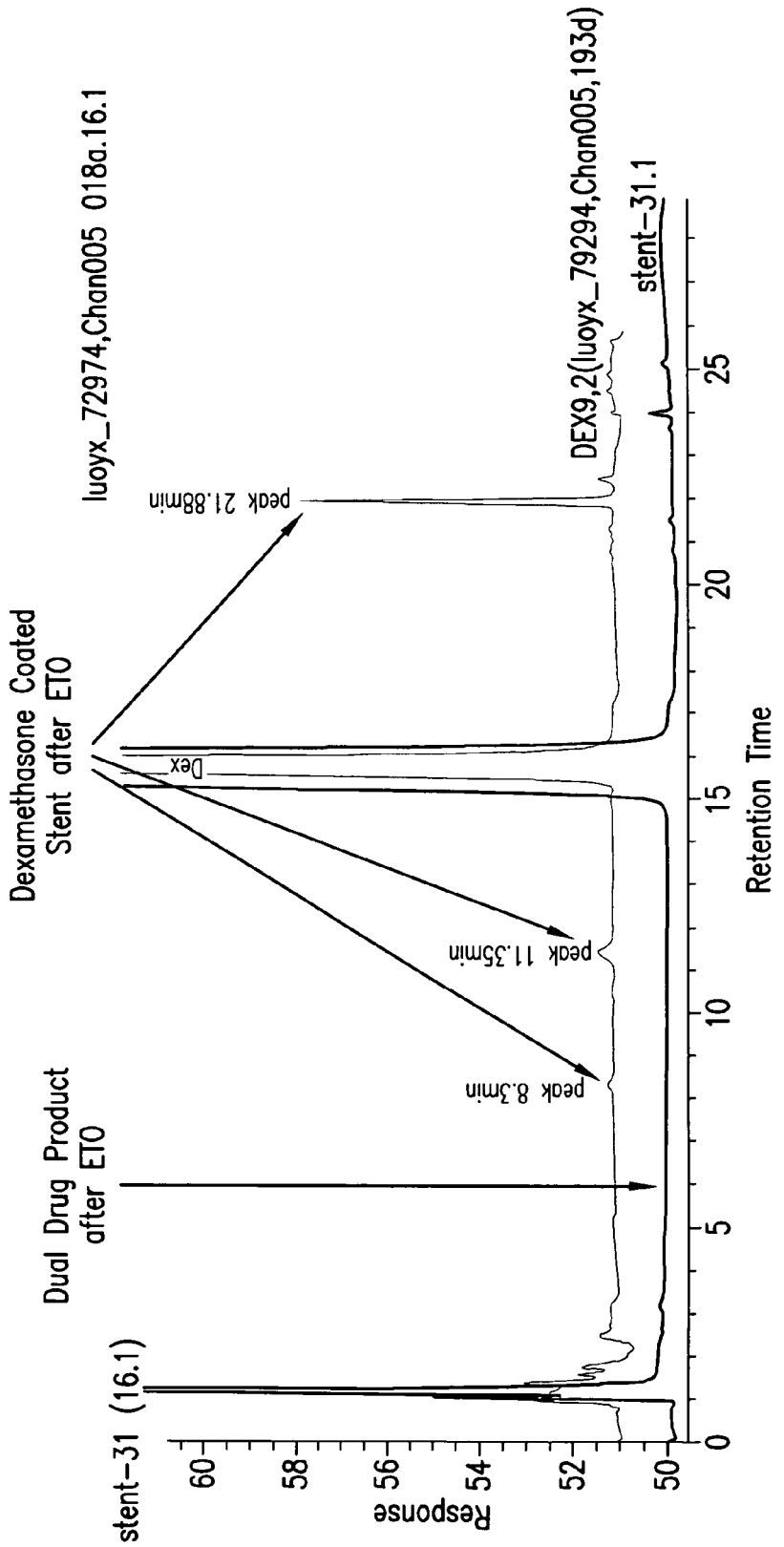
FIG. 16 shows the overlay of a chromatogram from a stent loaded with only dexamethasone and a chromatogram from a stent loaded with both dexamethasone and zotarolimus at a 1-to-1 ratio, according to embodiments of the invention.
Figure 17:
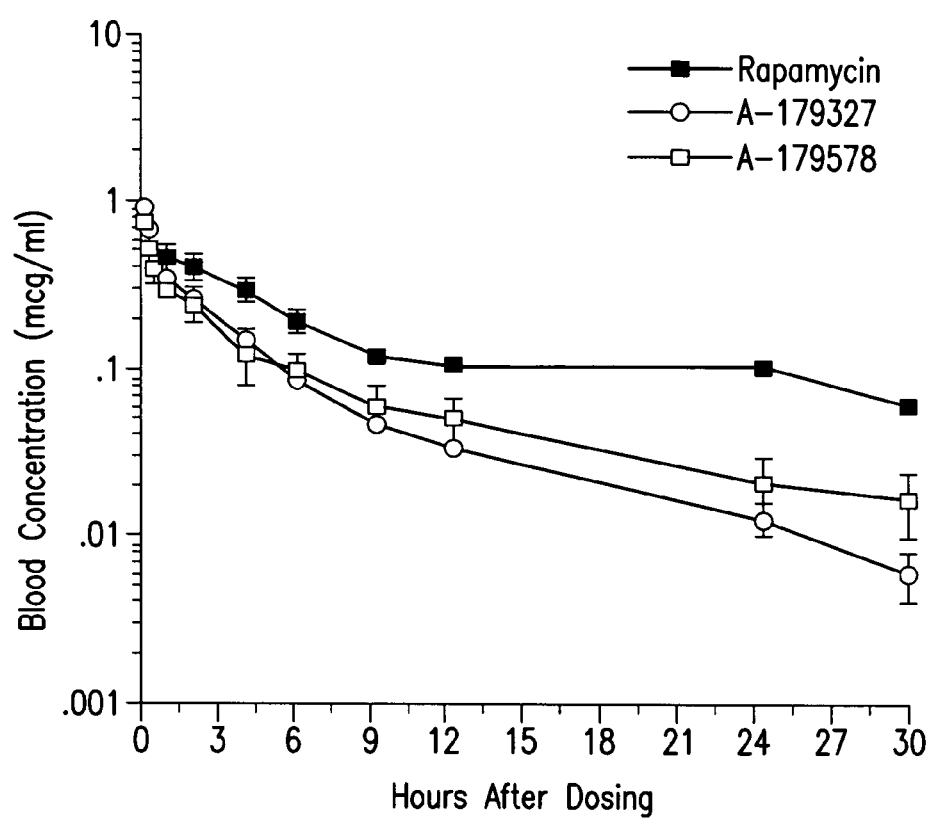
FIG. 17 shows blood concentrations±SEM (n=3) of tetrazole-containing rapamycin analogs dosed in monkeys, according to embodiments of the invention.
Figure 18:
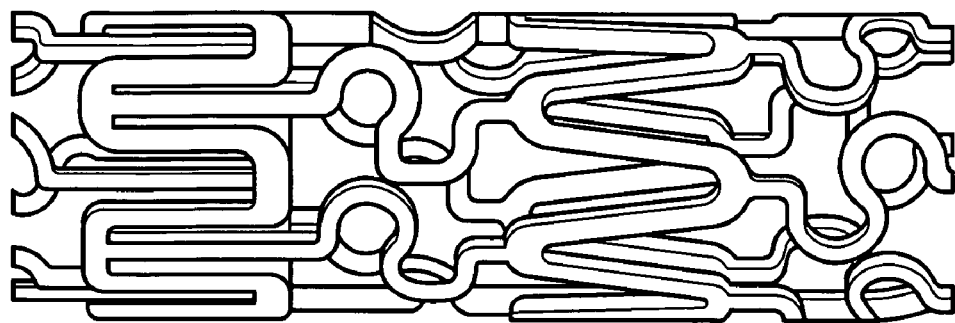
FIG. 18 is a side view in elevation showing a stent suitable for use in this invention, according to embodiments of the invention.
Figure 19B:
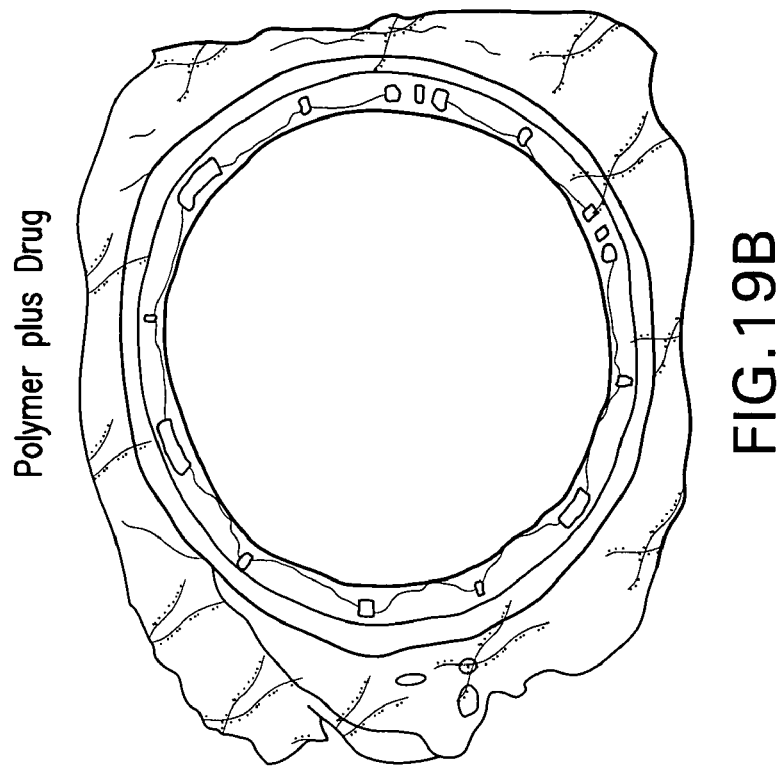
FIG. 19B is a cross-sectional view of a vessel segment in which was placed a stent coated with a polymer plus drug, according to embodiments of the invention.
Figure 19A:
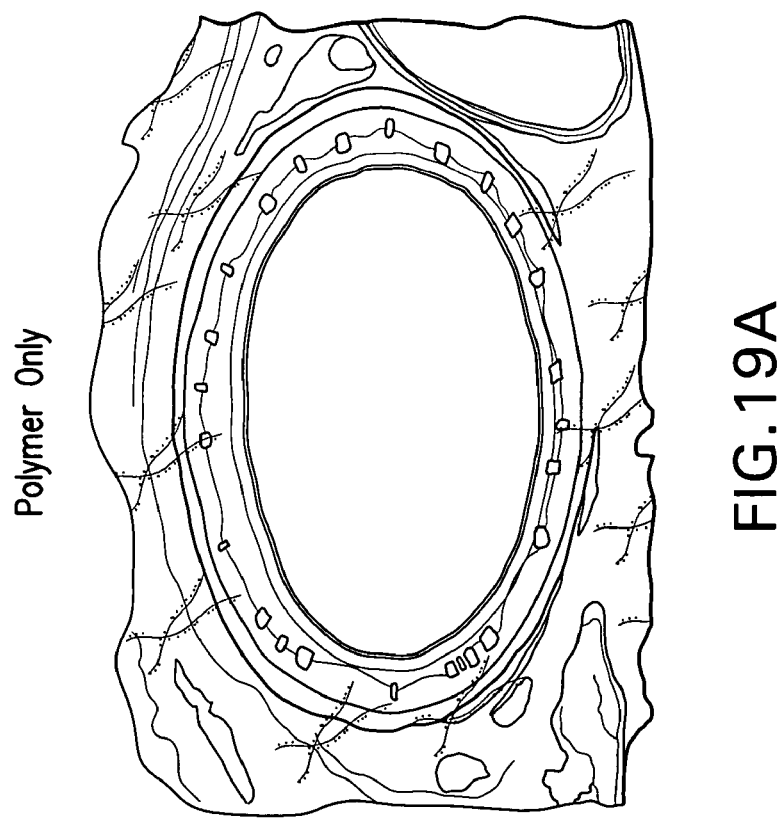
FIG. 19A is a cross-sectional view of a vessel segment in which was placed a stent coated with a polymer only, according to embodiments of the invention.

FIG. 16 shows the overlay of a chromatogram of a stent loaded with only dexamethasone and a chromatogram of a stent loaded with both dexamethasone and zotarolimus at a 1-to-1 ratio. As can be seen in the figure, dexamethasone in the dexamethasone-only coating degraded in the ETO sterilization environment with the production of at least three impurity peaks at 8.3, 11.3, and 21.8 minutes. In contrast, dexamethasone that was loaded in combination with zotarolimus in this same high humidity environment did not degrade. The impurity peaks seen in the dexamethasone-only coated stents were not present, nor were any impurity peaks evident in the chromatogram.

This figure thus demonstrates that zotarolimus acts a hydration inhibitor for the more hydrophilic dexamethasone, and that this inhibition has the effect of stabilizing the more hydrophilic drug dexamethasone in the presence of the less hydrophilic drug zotarolimus.

Preparation of Compound of the Invention

The compounds and processes of embodiments of the invention will be better understood in connection with the following synthetic schemes which illustrate the methods by which the compounds of the invention may be prepared.

The compounds of this invention may be prepared by a variety of synthetic routes. A representative procedure is shown in Scheme 1.

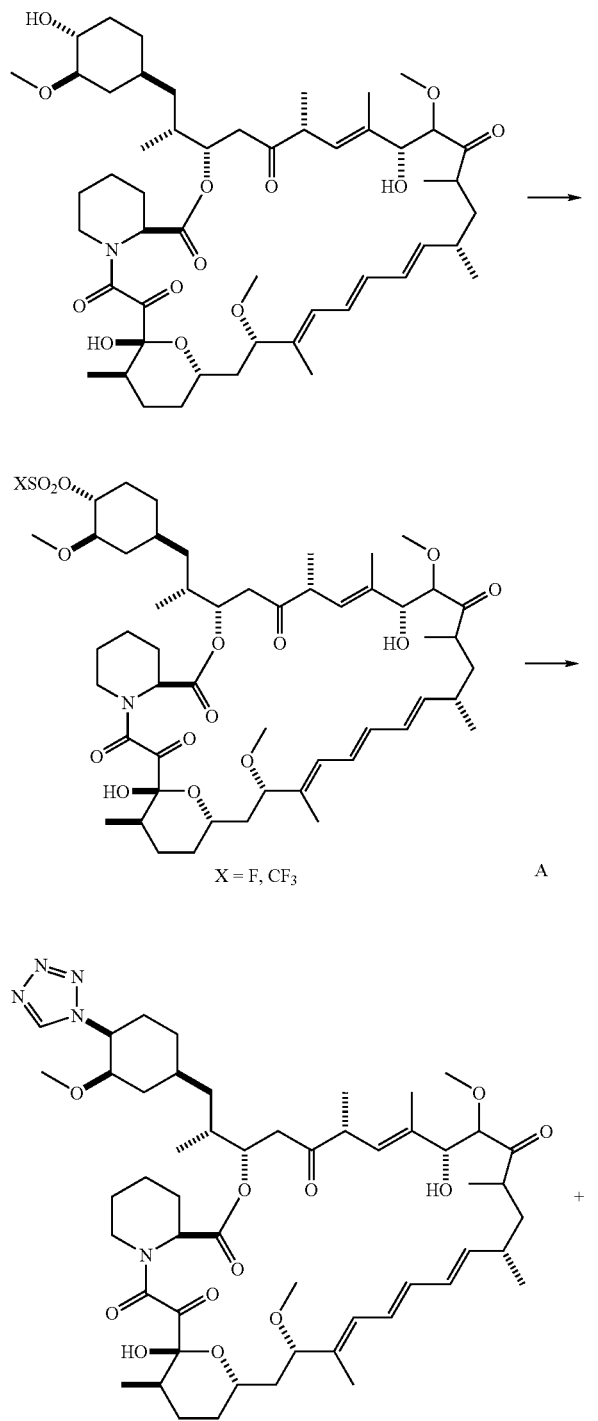

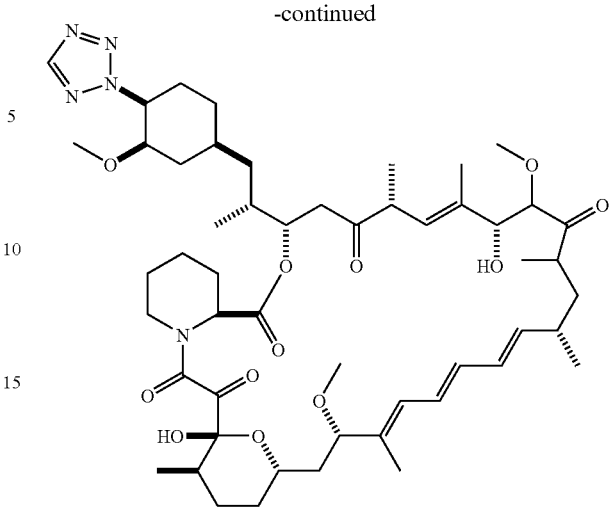

As shown in Scheme 1, conversion of the C-42 hydroxyl of rapamycin to a trifluoromethanesulfonate or fluorosulfonate leaving group provided A. Displacement of the leaving group with tetrazole in the presence of a hindered, non-nucleophilic base, such as 2,6-lutidine, or, preferably, diisopropylethyl amine provided epimers B and C, which were separated and purified by flash column chromatography.

Synthetic Methods

The foregoing may be better understood by reference to the following examples which illustrate the methods by which the compounds of the invention may be prepared and are not intended to limit the scope of the invention as defined in the appended claims.

Example 1

42-Epi-(tetrazolyl)-rapamycin (less polar isomer)

Example 1A

A solution of rapamycin (100 mg, 0.11 mmol) in dichloromethane (0.6 mL) at −78° C. under a nitrogen atmosphere was treated sequentially with 2,6-lutidine (53 uL, 0.46 mmol, 4.3 eq.) and trifluoromethanesulfonic anhydride (37 uL, 0.22 mmol), and stirred thereafter for 15 minutes, warmed to room temperature and eluted through a pad of silica gel (6 mL) with diethyl ether. Fractions containing the triflate were pooled and concentrated to provide the designated compound as an amber foam.

Example 1B

42-Epi-(tetrazolyl)-rapamycin (less polar isomer)

A solution of Example 1A in isopropyl acetate (0.3 mL) was treated sequentially with diisopropylethylamine (87 L, 0.5 mmol) and 1H-tetrazole (35 mg, 0.5 mmol), and thereafter stirred for 18 hours. This mixture was partitioned between water (10 mL) and ether (10 mL). The organics were washed with brine (10 mL) and dried ($Na_2SO_4$). Concentration of the organics provided a sticky yellow solid which was purified by chromatography on silica gel (3.5 g, 70-230 mesh) eluting with hexane (10 mL), hexane:ether (4:1(10 mL), 3:1(10 mL), 2:1(10 mL), 1:1(10 mL)), ether (30 mL), hexane:acetone (1:1(30 mL)). One of the isomers was collected in the ether fractions.

MS (ESI) m/e 966 (M)⁻;

Example 2

42-Epi-(tetrazolyl)-rapamycin (more polar isomer)

Example 2A

42-Epi-(tetrazolyl)-rapamycin (more polar isomer)

Collection of the slower moving band from the chromatography column using the hexane:acetone (1:1) mobile phase in Example 1B provided the designated compound.

MS (ESI) m/e 966 (M)⁻.

In vitro Assay of Biological Activity

The immunosuppressant activity of the compounds of the present invention was compared to rapamycin and two rapamycin analogs: 40-epi-N-[2'-pyridone]-rapamycin and 40-epi-N-[4'-pyridone]-rapamycin. The activity was determined using the human mixed lymphocyte reaction (MLR) assay described by Kino, T. et al. in *Transplantation Proceedings*, XIX(5):36-39, Suppl. 6 (1987). The results of the assay demonstrate that the compounds of the invention are effective immunomodulators at nanomolar concentrations, as shown in Table 1.

TABLE 1

| Example | Human MLR IC$_{50}$ ± S.E.M. (nM) |
| --- | --- |
| Rapamycin | 0.91 ± 0.36 |
| 2-pyridone | 12.39 ± 5.3 |
| 4-pyridone | 0.43 ± 0.20 |
| Example 1 | 1.70 ± 0.48 |
| Example 2 | 0.66 ± 0.19 |

The pharmacokinetic behaviors of Example 1 and Example 2 were characterized following a single 2.5 mg/kg intravenous dose in cynomolgus monkey (n=3 per group). Each compound was prepared as 2.5 mg/mL solution in a 20% ethanol:30% propylene glycol:2% cremophor EL:48% dextrose 5% in water vehicle. The 1 mL/kg intravenous dose was administered as a slow bolus (1-2 minutes) in a saphenous vein of the monkeys. Blood samples were obtained from a femoral artery or vein of each animal prior to dosing and 0.1 (IV only), 0.25, 0.5, 1, 1.5, 2, 4, 6, 9, 12, 24, and 30 hours after dosing. The EDTA preserved samples were thoroughly mixed and extracted for subsequent analysis.

An aliquot of blood (1.0 mL) was hemolyzed with 20% methanol in water (0.5 ml) containing an internal standard. The hemolyzed samples were extracted with a mixture of ethyl acetate and hexane (1:1 (v/v), 6.0 mL). The organic layer was evaporated to dryness with a stream of nitrogen at room temperature. Samples were reconstituted in methanol:water (1:1, 150 μL). The title compounds (50 μL injection) were separated from contaminants using reverse phase HPLC with UV detection. Samples were kept cool (4° C.) through the run. All samples from each study were analyzed as a single batch on the HPLC.

Area under the curve (AUC) measurements of Example 1, Example 2 and the internal standard were determined using the Sciex MacQuan™ software. Calibration curves were derived from peak area ratio (parent drug/internal standard) of the spiked blood standards using least squares linear regression of the ratio versus the theoretical concentration. The methods were linear for both compounds over the range of the standard curve (correlation>0.99) with an estimated quantitation limit of 0.1 ng/mL. The maximum blood concentration ($C_{MAX}$) and the time to reach the maximum blood concentration ($T_{MAX}$) were read directly from the observed blood concentration-time data. The blood concentration data were submitted to multi-exponential curve fitting using CSTRIP to obtain estimates of pharmacokinetic parameters. The estimated parameters were further defined using NONLIN84. The area under the blood concentration-time curve from 0 to t hours (last measurable blood concentration time point) after dosing ($AUC_{0-t}$) was calculated using the linear trapeziodal rule for the blood-time profiles. The residual area extrapolated to infinity, determined as the final measured blood concentration ($C_t$) divided by the terminal elimination rate constant (β), and added to $AUC_{0-t}$ to produce the total area under the curve ($AUC_{0-t}$).

As shown in FIG. 1 and Table 2, both Example 1 and Example 2 had a surprisingly substantially shorter terminal elimination half-life ($t_{1/2}$) when compared to rapamycin. Thus, only the compounds of the invention provide both sufficient efficacy (Table 1) and a shorter terminal half-life (Table 2).

TABLE 2

| Compound | AUC ng · hr/mL | $t_{1/2}$ (hours) |
| --- | --- | --- |
| Rapamycin | 6.87 | 16.7 |
| 2-pyridone | 2.55 | 2.8 |
| 4-pyridone | 5.59 | 13.3 |
| Example 1 | 2.35 | 5.0 |
| Example 2 | 2.38 | 6.9 |

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A system for delivering a lipophilic agent to a desired area outside a body lumen in order to treat a disease manifesting itself in the body lumen or in organs connected to the body lumen, or to maintain patency of the body lumen, comprising:
    a medical device;
    a first lipophilic agent capable of penetrating the body lumen wherein the transfer coefficient of said first lipophilic agent is by an amount of at least 5,000 (μg/mL)⁻¹, wherein said first lipophilic agent comprises zotarolimus having one of the following structures:

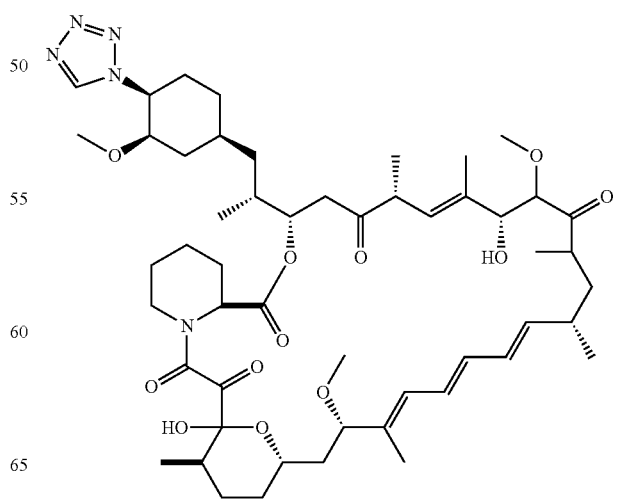

-continued

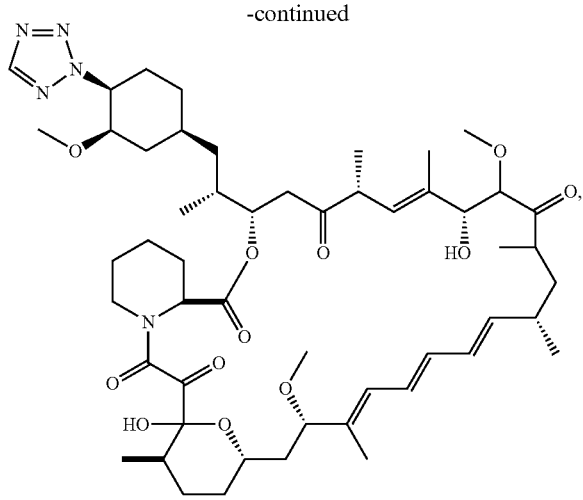

wherein said first lipophilic agent/medical device is placed adjacent to said body lumen; and
wherein a therapeutically effective amount of said first lipophilic agent is delivered via the medical device to a desired area outside the body lumen where the medical device is placed within a subject.

2. The system according to claim 1, further comprising at least one pharmaceutically acceptable carrier or excipient, wherein said medical device is connected to said pharmaceutically acceptable carrier or excipient.

3. The system according to claim 2, wherein said pharmaceutically acceptable carrier or excipient is a polymer.

4. The system according to claim 2, wherein said pharmaceutically acceptable carrier or excipient is an agent.

5. The system according to claim 1, wherein said body lumen comprises at least one of a vessel wall, a coronary artery, esophageal lumen, and a urethra.

6. The system according to claim 5, wherein said first lipophilic agent/medical device is placed adjacent to said body, wherein a therapeutically effective amount of said first lipophilic agent is delivered into said coronary arteries and diffused into the pericardial sac in said drug delivery system.

7. The system according to claim 6, wherein said system provides substantially uniform drug delivery of said lipophilic agent to the myocardium.

8. The system according to claim 6, wherein said system is useful for the treatment of vascular diseases in a subject.

9. The system according to claim 3, wherein said delivery mechanism of said first lipophilic agent includes polymer hydration followed by dissolution of said first lipophilic agent, and wherein said first lipophilic agent is thereafter delivered into said body lumen.

10. The system according to claim 3, wherein said delivery mechanism of said first lipophilic agent includes a lipophilic agent/polymer matrix which controls the elution rate of said first lipophilic agent to said body lumen.

11. The system according to claim 1, further comprises at least one second lipophilic agent.

12. The system according to claim 1, further comprises at least one lipophilic prodrug.

13. The system according to claim 1, further comprises at least one lipophilic penetration enhancer.

14. The system according to claim 13, wherein said lipophilic penetration enhancer is a pharmaceutical agent.

15. The system according to claim 11, wherein the concentration of said second lipophilic agent in combination with said first lipophilic agent is a therapeutically effective amount.

16. The system according to claim 1, further comprises at least one beneficial agent selected from the group consisting of antithrombotics, anticoagulents, antiplatelet agents, anti-ulcer/antireflux agents, antinauseants/antiemetics and thrombolytic agents.

17. The system according to claim 1, wherein the dosage delivery of said first lipophilic agent into said body lumen ranges from about 15 μg/g to about 150 μg/g over a period of up to 5 days.

18. The system according to claim 1, wherein the dosage delivery of said first lipophilic agent into said body lumen ranges from about 15 μg/g to about 80 μg/g over a period from about 5 days to about 15 days.

19. The system according to claim 1, wherein the dosage delivery of said first lipophilic agent into said body lumen ranges from about 5 μg/g to about 60 μg/g over a period from 15 days to about 28 days.

20. The system according to claim 1, wherein said first lipophilic agent reaches therapeutically significant concentrations in targeted areas in said subject comprising at least one of the distal myocardium, the unstented myocardium, in said subjacent myocardium, in unstented and distal coronary arteries, and maintains those concentrations throughout a 28 day period.

21. The system according to claim 1, wherein said medical device is permanently or temporarily implanted into a subject.

22. The system according to claim 1, wherein said first lipophilic agent is in amorphous form.

23. The system according to claim 1, further comprises a beneficial agent including at least one of antithrombotics, anticoagulants, antiplatelets agents, anti-lipid agents, thrombolytics, antiproliferatives, antiinflammatories, agents that inhibit hyperplasia, smooth muscle cell inhibitors antibiotics, growth factor inhibitors, cell adhesion inhibitors, cell adhesion promoters, antimitotics, antifibrins, antioxidants, antineoplastics, agents that promote endothelial cell recovery, matrix metalloproteinase inhibitors, antimetabolites, antiallergic substances, viral vectors, nucleic acids, monoclonal antibodies, inhibitors of tyrosine kinase, antisense compounds, oligionucleotides, cell permeation enhancers, and anycombinations thereof.

24. The system according to claim 1, further comprises a beneficial agent including at least one of hypoglycemic agents, hypolipidemic agents, proteins, nucleic acids, agents useful for erythropoiesis stimulation, angiogenesis agents, antiulcer/antireflux agents, and antinauseants/antiemetics, PPAR-alpha agonists, and any combinations thereof.

25. The system according to claim 1, further comprises a beneficial agent including at least one of sodium heparin, LMW heparins, heparoids, hirudin, argatroban, forskolin, vapriprost, prostacyclin and prostacylin analogues, dextran, D-phe-pro-arg-chloromethylketone (synthetic antithrombin), glycoprotein IIba/IIa (platelet membrane receptor antagonist antibody), recombinant hirudin, thrombin inhibitors, indomethacin, phenyl salicylate, β-estradiol, vinblastine, ABT-627 (astrasentan), testosterone, progesterone, paclitaxel, methotrexate, fotemusine, RPR-101511A, cyclosporine A, vincristine, carvediol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, iotrolan and any combinations thereof.

26. The system according to claim 1, wherein said medical device is an endovascular medical device.

27. The system according to claim 1, wherein said medical device includes intracoronary medical devices selected from the group consisting of stents, drug delivery catheters, grafts, and drug delivery balloons utilized in subjects' vasculature.

28. The system according to claim 1, wherein said medical device includes a stent selected from the group consisting of peripheral stents, peripheral coronary stents, degradable coronary stents, non-degradable coronary stents, self-expanding stents, balloon-expanded stents, and esophageal stents.

29. The system according to claim 1, wherein said medical device is selected from the group consisting of arterio-venous grafts, by-pass grafts, penile implants, vascular implants and grafts, intravenous catheters, small diameter grafts, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

30. The system according to claim 1, wherein said medical device is selected from the group consisting of pacemakers, vascular grafts, sphincter devices, urethral devices, bladder devices, renal devices, gastroenteral and anastomotic devices, vertebral disks, hemostatic barriers, clamps surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue adhesives, tissue sealants, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuro aneurysm treatment coils, hemodialysis devices, uterine bleeding patches, anastomotic closures, in vitro diagnostics, aneurysm exclusion devices, neuropatches, vena cava filters, urinary dilators, endoscopic surgical and wound drainings, surgical tissue extractors, transition sheaths and dialators, coronary and peripheral guidewires, circulatory support systems, tympanostomy vent tubes, cerebrospinal fluid shunts, defibrillator leads, percutaneous closure devices, drainage tubes bronchial tubes, vascular coils, vascular protection devices, vascular intervention devices, including vscular filters and distal supoort devices and emboli filter/entrapment aids, AV access grafts, surgical tampons, drug delivery capsule and cardiac valves.

31. The system according to claim 1, wherein said medical device is selected from the group consisting of atrial septal defect closures, electro-stimulation leads for cardiac rhythm management, tissue and mechanical prosthetic heart valves and rings, arterial-venous shunts, valve annuloplasty devices, mitral valve repair devices, left ventricle assist devices, left atrial appendage filters, cardiac sensors, pacemaker electrodes and leads.

32. The system according to claim 1, wherein said lipophilic agent is continuously delivered to the epicardium and/or pericardial sac.

33. The system according to claim 1, wherein said lipophilic agent comprises zotarolimus having both structures of claim 1.

* * * * *